United States Patent
Jackson et al.

(10) Patent No.: US 10,981,009 B2
(45) Date of Patent: Apr. 20, 2021

(54) LATENCY-BASED ADAPTATION OF ANTI-TACHYARRHYTHMIA PACING THERAPY

(71) Applicant: Medtronic, Inc., Minneapolis, MN (US)

(72) Inventors: Troy E. Jackson, Rogers, MN (US); Vincent P. Ganion, Andover, MA (US)

(73) Assignee: MEDTRONIC, INC., Minneapolis, MN (US)

( * ) Notice: Subject to any disclaimer, the term of this patent is extended or adjusted under 35 U.S.C. 154(b) by 113 days.

(21) Appl. No.: 16/268,941

(22) Filed: Feb. 6, 2019

(65) Prior Publication Data
US 2019/0167994 A1    Jun. 6, 2019

Related U.S. Application Data

(63) Continuation of application No. 15/141,741, filed on Apr. 28, 2016, now Pat. No. 10,201,710.

(51) Int. Cl.
*A61N 1/362* (2006.01)
*A61N 1/05* (2006.01)
*A61N 1/37* (2006.01)
*A61N 1/375* (2006.01)
*A61N 1/39* (2006.01)

(52) U.S. Cl.
CPC ............. *A61N 1/3622* (2013.01); *A61N 1/05* (2013.01); *A61N 1/056* (2013.01); *A61N 1/3621* (2013.01); *A61N 1/3712* (2013.01); *A61N 1/3756* (2013.01); *A61N 1/3962* (2013.01)

(58) Field of Classification Search
CPC ........ A61N 1/3622; A61N 1/05; A61N 1/056; A61N 1/3621; A61N 1/3712; A61N 1/3756; A61N 1/3962
See application file for complete search history.

(56) References Cited

U.S. PATENT DOCUMENTS

| | | |
|---|---|---|
| 5,117,824 A | 6/1992 | Keimel et al. |
| 5,271,393 A | 12/1993 | Callaghan |
| 5,545,186 A | 8/1996 | Olson et al. |
| 5,755,736 A | 5/1998 | Gillberg et al. |

(Continued)

OTHER PUBLICATIONS

Jackson et al., "Latency-Based Adaptation of Anti-Tachyarrhythmia Pacing Therapy", EP Application No. 17721021.8; EP Communication pursuant to Article 94(3) dated Feb. 24, 2020, 5 pages.

(Continued)

*Primary Examiner* — Lindsey G Wehrheim
(74) *Attorney, Agent, or Firm* — Shumaker & Sieffert, P.A.

(57) ABSTRACT

A medical device comprises therapy delivery circuitry and processing circuitry. The therapy delivery circuitry is configured to deliver anti-tachycardia pacing (ATP) therapy to a heart of a patient. The ATP therapy includes one or more pulse trains and each of the one or more pulse trains includes a plurality of pacing pulses. The processing circuitry is configured to, for at least one of the plurality of pacing pulses of at least one of the one or more pulse trains, determine at least one latency metric of an evoked response of the heart to the pacing pulse. The processing circuitry is further configured to modify the ATP therapy based on the at least one latency metric.

38 Claims, 18 Drawing Sheets

(56) References Cited

U.S. PATENT DOCUMENTS

| | | |
|---|---|---|
| 5,855,592 A | 1/1999 | McGee et al. |
| 6,167,308 A | 12/2000 | DeGroot |
| 6,292,691 B1 | 9/2001 | Pendekanti et al. |
| 6,775,572 B2 | 8/2004 | Zhu et al. |
| 6,892,094 B2 | 5/2005 | Ousdigian et al. |
| 7,181,275 B2 | 2/2007 | Havel |
| 7,363,081 B1 | 4/2008 | Kroll et al. |
| 7,376,464 B2 | 5/2008 | Zhu et al. |
| 7,515,960 B2 | 4/2009 | Sharma |
| 7,684,862 B2 | 3/2010 | Belk et al. |
| 7,761,153 B2 | 7/2010 | Belk et al. |
| 7,761,155 B2 | 7/2010 | Belk et al. |
| 7,792,578 B2 | 9/2010 | Belk et al. |
| 7,792,579 B2 | 9/2010 | Belk et al. |
| 7,894,899 B2 | 2/2011 | Sharma |
| 8,064,999 B2 | 11/2011 | Jackson et al. |
| 8,706,221 B2 | 4/2014 | Belk et al. |
| 8,744,572 B1 | 6/2014 | Greenhut |
| 8,923,963 B2 | 12/2014 | Bonner et al. |
| 9,795,789 B2 | 10/2017 | Kaiser |
| 10,201,710 B2 * | 2/2019 | Jackson ............... A61N 1/3756 |
| 2003/0083703 A1 | 5/2003 | Zhu et al. |
| 2005/0075676 A1 * | 4/2005 | Deno .................... A61N 1/365 607/9 |
| 2012/0316613 A1 | 12/2012 | Keefe et al. |
| 2014/0121720 A1 | 5/2014 | Bonner et al. |
| 2014/0276928 A1 | 9/2014 | Vanderpool et al. |
| 2015/0297905 A1 | 10/2015 | Greenhut et al. |
| 2015/0305641 A1 | 10/2015 | Stadler et al. |

OTHER PUBLICATIONS (PCT/US2017/029251) PCT Notification of Transmittal of the International Search Report and the Written Opinion of the International Searching Authority, dated Jul. 12, 2017, 12 pages.

U.S. Appl. No. 13/665,601, by Medtronic (Inventors: Bonner et al.), filed Oct. 31, 2012.

Prosecution History from U.S. Appl. No. 15/141,741, dated Mar. 26, 2018 through Oct. 11, 2018, 41 pp.

European Communication dated Oct. 13, 2020, corresponding to counterpart, European Patent Application No. 17721021.8; 4 pages.

* cited by examiner

LATENCY-BASED ADAPTATION OF ANTI-TACHYARRHYTHMIA PACING THERAPY This application is a continuation of U.S. patent application Ser. No. 15/141,741, filed Apr. 28, 2016, entitled "LATENCY-BASED ADAPTATION OF ANTI-TACHYARRHYTHMIA PACING THERAPY," now U.S. Pat. No. 10,201,710, the entire content of which is incorporated by reference herein.

TECHNICAL FIELD

The disclosure relates to medical devices configured to detect and treat cardiac arrhythmias with anti-tachyarrhythmia pacing (ATP) therapy.

BACKGROUND

Implantable cardioverter defibrillators (ICDs) and implantable artificial pacemakers may provide cardiac pacing therapy to a patient's heart when the natural pacemaker and/or conduction system of the heart fails to provide synchronized atrial and ventricular contractions at rates and intervals sufficient to sustain healthy patient function. Such antibradycardial pacing may provide relief from symptoms, or even life support, for a patient. Cardiac pacing may also provide electrical overdrive stimulation, e.g., ATP therapy, to suppress or convert tachyarrhythmias, again supplying relief from symptoms and preventing or terminating arrhythmias that could lead to sudden cardiac death.

SUMMARY

ATP therapy may be delivered with decreasing time intervals between pulses, to advance the heart to refractory. However, decreasing the time interval between pulses can also lead to loss of capture and may result in delivery of wasteful pulses, as well as waste of time to successful termination of the tachyarrhythmia. Traditional ATP therapy systems may wait for an indication of loss of capture before adapting the delivery of ATP therapy. The systems and methods described herein may be used to modify ATP therapy before loss of capture occurs to prevent loss of capture, prevent delivery of unnecessary pulses, and shorten the time to successful termination of the tachyarrhythmia.

In one example, this disclosure is directed to a method comprising delivering anti-tachycardia pacing (ATP) therapy to a heart of a patient, the ATP therapy including one or more pulse trains, each of the one or more pulse trains including a plurality of pacing pulses. The method further comprises, for at least one of the plurality of pacing pulses of at least one of the one or more pulse trains, determining at least one latency metric of an evoked response of the heart to the pacing pulse. The method further comprises modifying the ATP therapy based on the at least one latency metric.

In another example, this disclosure is directed to a medical device comprising therapy delivery circuitry and processing circuitry. The therapy delivery circuitry is configured to deliver anti-tachycardia pacing (ATP) therapy to a heart of a patient. The ATP therapy includes one or more pulse trains and each of the one or more pulse trains includes a plurality of pacing pulses. The processing circuitry is configured to, for at least one of the plurality of pacing pulses of at least one of the one or more pulse trains, determine at least one latency metric of an evoked response of the heart to the pacing pulse. The processing circuitry is further configured to modify the ATP therapy based on the at least one latency metric.

In a further example, this disclosure is directed to a non-transitory computer-readable storage medium having stored thereon instructions that, when executed, cause a processor to control a therapy delivery circuitry to deliver anti-tachycardia pacing (ATP) therapy to a heart of a patient. The ATP therapy includes one or more pulse trains and each of the one or more pulse trains includes a plurality of pacing pulses. The instructions, when executed, further cause the processor to, for at least one of the plurality of pacing pulses of at least one of the one or more pulse trains, determine at least one latency metric of an evoked response of the heart to the pacing pulse. The instructions, when executed, further cause the processor to modify the ATP therapy based on the at least one latency metric.

In a further example, this disclosure is directed to a system comprises a first implantable medical device and a second implantable medical device. The first implantable medical device is configured to deliver anti-tachycardia pacing (ATP) therapy to a heart of a patient. The ATP therapy includes one or more pulse trains and each of the one or more pulse trains includes a plurality of pacing pulses. At least one of the first implantable medical device or the second implantable medical device is further configured to, for at least one of the plurality of pacing pulses of at least one of the one or more pulse trains, determine at least one latency metric of the evoked response of the heart to the pacing pulse. The first implantable medical device is configured modify the ATP therapy based on the at least one latency metric.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

Figure 1A:
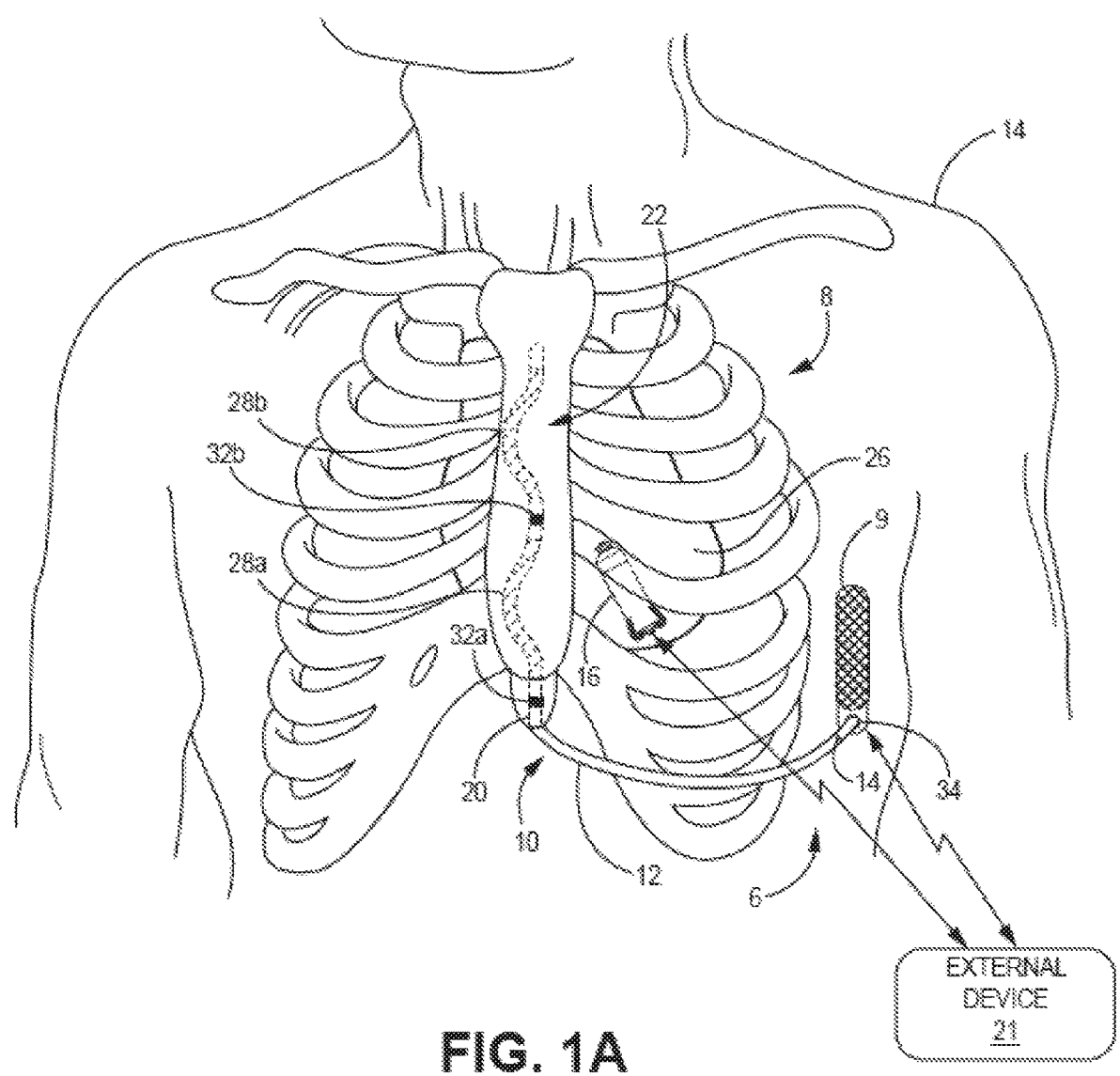
FIG. 1A is a front view of a patient implanted with an example implantable medical device system.
Figure 1B:
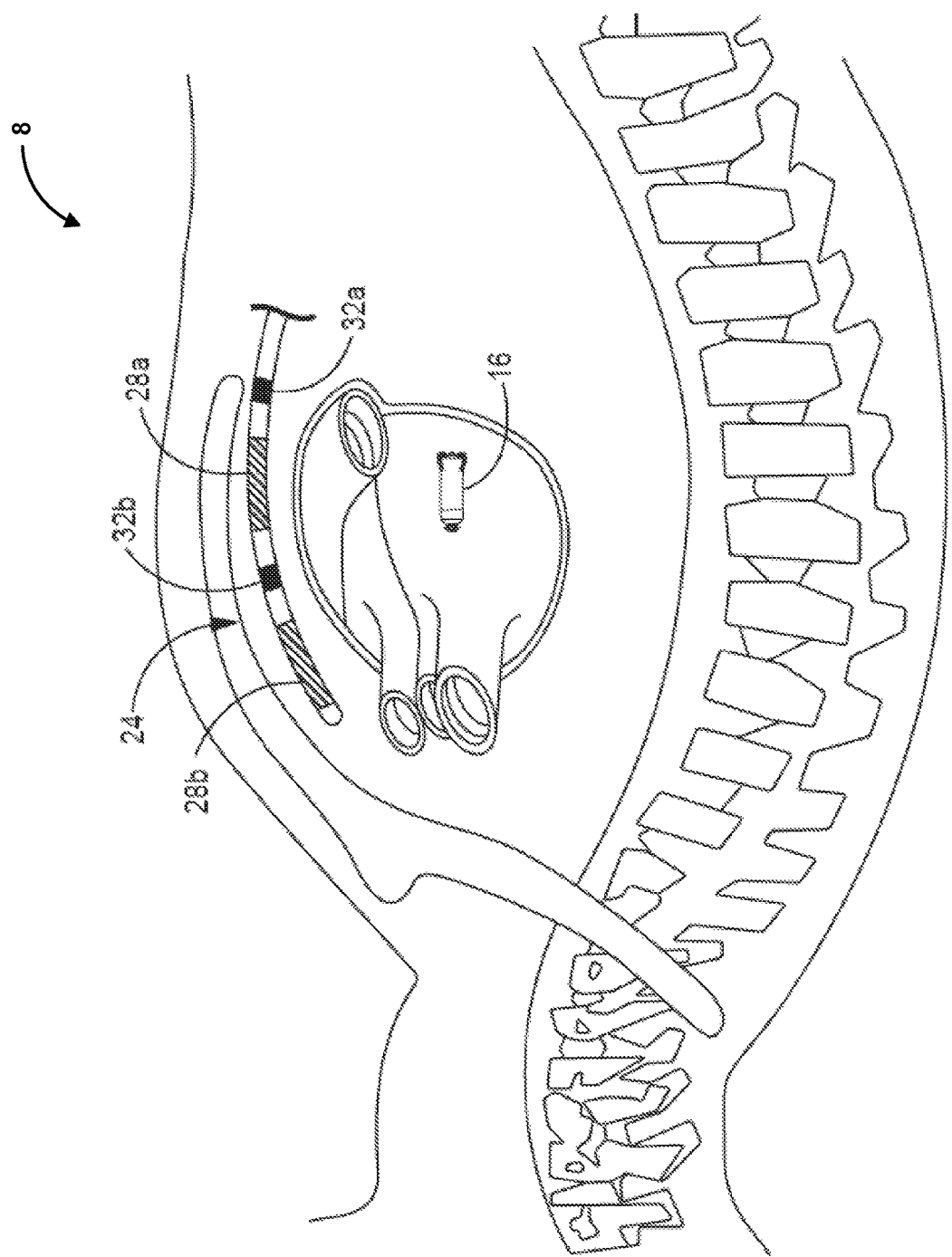
FIG. 1B is a side view of the patient implanted with the implantable medical device system of FIG. 1A.
Figure 1C:
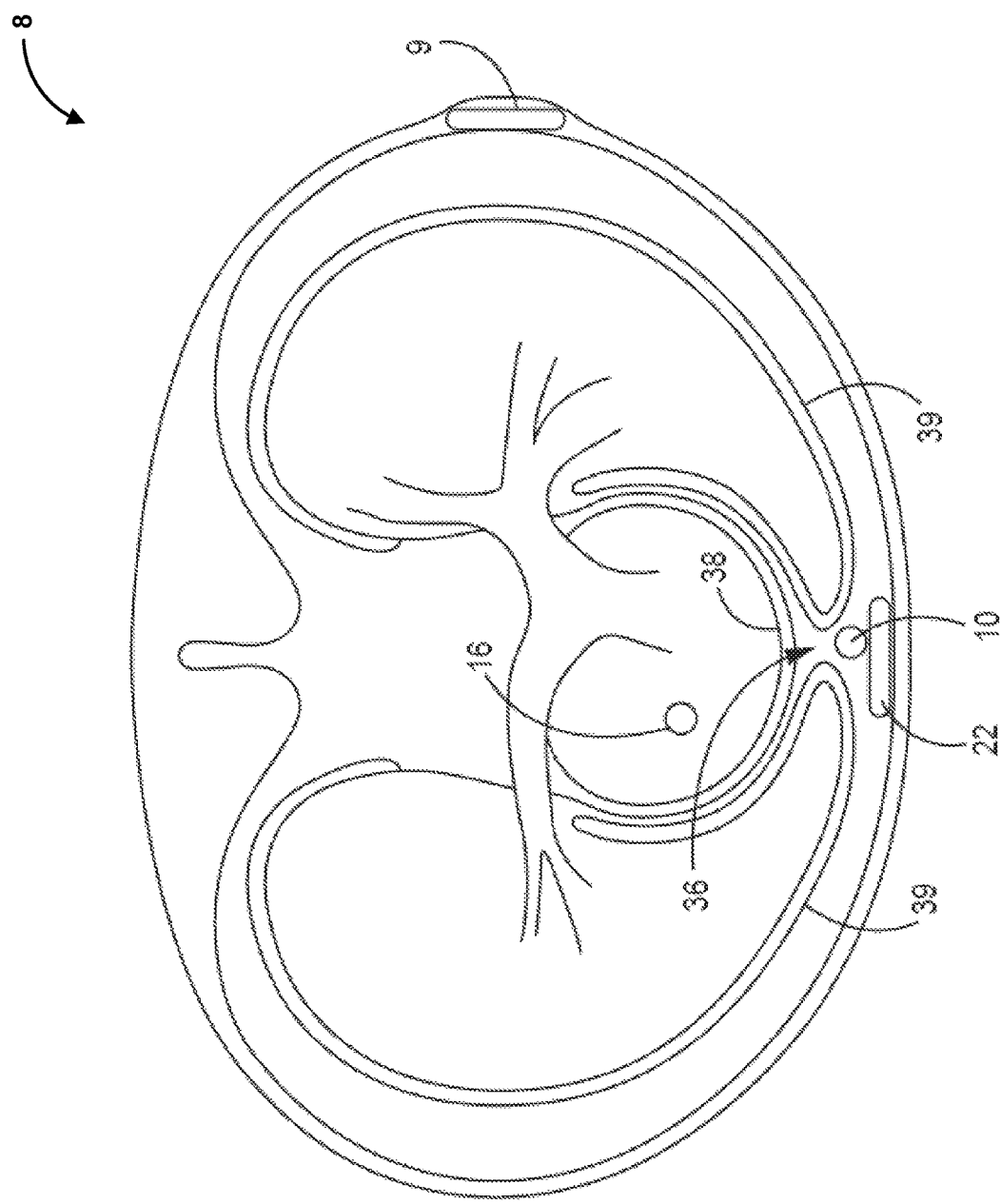
FIG. 1C is a transverse view the patient implanted with the implantable medical device system of FIGS. 1A and 1B.

FIGS. 1A-1C are conceptual diagrams illustrating various views of an example implantable medical device system 8. The system 8 includes an extracardiovascular ICD system 6, including ICD 9 connected to a medical electrical lead 10, and IPD 16 constructed in accordance with the principles of the present application. FIG. 1A is a front view of a patient 14 implanted with the medical device system 8. FIG. 1B is a side view of patient 14 implanted with the medical device system 8. FIG. 1C is a transverse view of patient 14 implanted with the medical device system 8.

The ICD 9 may include a housing that forms a hermetic seal that protects components of the ICD 9. The housing of the ICD 9 may be formed of a conductive material, such as titanium or titanium alloy, which may function as a housing electrode (sometimes referred to as a can electrode). In other examples, the ICD 9 may be formed to have or may include one or more electrodes on the outermost portion of the housing. The ICD 9 may also include a connector assembly (also referred to as a connector block or header) that includes electrical feedthroughs through which electrical connections are made between conductors of lead 10 and electronic components included within the housing of the ICD 9. As will be described in further detail herein, housing may house one or more processors, memories, transmitters, receivers, sensors, sensing circuitry, therapy delivery circuitry, power sources and other appropriate components. The housing is configured to be implanted in a patient, such as patient 14.

ICD 9 is implanted extra-thoracically on the left side of patient 14, e.g., under the skin and outside the ribcage (subcutaneously or submuscularly). ICD 9 may, in some instances, be implanted between the left posterior axillary line and the left anterior axillary line of patient 14. ICD 9 may, however, be implanted at other extra-thoracic locations on patient 14 as described later.

Lead 10 may include an elongated lead body 12 sized to be implanted in an extracardiovascular location proximate the heart, e.g., intra-thoracically (as illustrated in FIGS. 1A-C), or subcutaneously. In the illustrated example, lead body 12 extends superiorly intra-thoracically underneath the sternum, in a direction substantially parallel to the sternum. In one example, the distal portion 24 of lead 10 may reside in a substernal location such distal portion 24 of lead 10 extends superior along the posterior side of the sternum substantially within the anterior mediastinum 36. Anterior mediastinum 36 may be viewed as being bounded laterally by pleurae 39, posteriorly by pericardium 38, and anteriorly by the sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), adipose tissue, some lymph vessels, lymph glands, substernal musculature (e.g., transverse thoracic muscle), the thymus gland, branches of the internal thoracic artery, and the internal thoracic vein. Lead 10 may be implanted at other locations, such as over the sternum, offset to the right of the sternum, angled lateral from the proximal or distal end of the sternum, or the like.

Lead body 12 may have a generally tubular or cylindrical shape and may define a diameter of approximately 3-9 French (Fr), however, lead bodies of less than 3 Fr and more than 9 Fr may also be utilized. In another configuration, lead body 12 may have a flat, ribbon, or paddle shape with solid, woven filament, or metal mesh structure, along at least a portion of the length of lead body 12. In such an example, the width across lead body 12 may be between 1-3.5 mm. Other lead body designs may be used without departing from the scope of this application.

Lead body 12 of lead 10 may be formed from a non-conductive material, including silicone, polyurethane, fluoropolymers, mixtures thereof, and other appropriate materials, and shaped to form one or more lumens (not shown), however, the techniques are not limited to such constructions. Distal portion 24 may be fabricated to be biased in a desired configuration, or alternatively, may be manipulated by the user into the desired configuration. For example, distal portion 24 may be composed of a malleable material such that the user can manipulate distal portion 24 into a desired configuration where it remains until manipulated to a different configuration.

Lead body 12 may include a proximal end 14 and a distal portion 24 configured to deliver electrical energy to the heart or sense electrical energy of the heart. Distal portion 24 may be anchored to a desired positioned within the patient, for example, substernally or subcutaneously by, for example, suturing distal portion 24 to the patient's musculature, tissue, or bone at the xiphoid process entry site. Alternatively, distal portion 24 may be anchored to the patient or through the use of rigid tines, prongs, barbs, clips, screws, and/or other projecting elements or flanges, disks, pliant tines, flaps, porous structures such as a mesh-like element and metallic or non-metallic scaffolds that facilitate tissue growth for engagement, bio-adhesive surfaces, and/or any other non-piercing elements.

Distal portion 24 includes defibrillation electrode 28 configured to deliver a cardioversion/defibrillation shock to the patient's heart. Defibrillation electrode 28 may include a plurality of sections or segments 28a and 28b spaced a distance apart from each other along the length of distal portion 24. The defibrillation electrode segments 28a and 28b may be a disposed around or within lead body 12 of distal portion 24, or alternatively, may be embedded within the wall of lead body 12. In one configuration, defibrillation electrode segments 28a and 28b may be a coil electrode formed by a conductor. The conductor may be formed of one or more conductive polymers, ceramics, metal-polymer composites, semiconductors, metals or metal alloys, including but not limited to, one of or a combination of the platinum, tantalum, titanium, niobium, zirconium, ruthenium, indium, gold, palladium, iron, zinc, silver, nickel, aluminum, molybdenum, stainless steel, MP35N, carbon, copper, polyaniline, polypyrrole and other polymers. In another configuration, each of the defibrillation electrodes segments 28a and 28b may be a flat ribbon electrode, a paddle electrode, a braided or woven electrode, a mesh electrode, a directional electrode, a patch electrode or another type of electrode configured to deliver a cardioversion/defibrillation shock to the patient's heart.

In one configuration, the defibrillation electrode segments 28a and 28b are spaced approximately 0.25-4.5 cm, and in some instances between 1-3 cm apart from each other. In another configuration, the defibrillation electrode segments 28a and 28b are spaced approximately 0.25-1.5 cm apart from each other. In a further configuration, the defibrillation electrode segments 28a and 28b are spaced approximately 1.5-4.5 cm apart from each other. In the configuration shown in FIGS. 1A-1C, the defibrillation electrode segments 28a and 28b span a substantial part of distal portion 24. Each of the defibrillation electrode segments 28a and 28b may be between approximately 1-10 cm in length and, more preferably, between 2-6 cm in length and, even more preferably, between 3-5 cm in length. However, lengths of greater than 10 cm and less than 1 cm may be utilized without departing from the scope of this disclosure. A total length of defibrillation electrode 28 (e.g., length of the two segments 28a and 28b combined) may vary depending on a number of variables. The defibrillation electrode 28 may, in one example, have a total length of between approximately 5-10 cm. However, the defibrillation electrode segments 28a and 28b may have a total length less than 5 cm and greater than 10 cm in other examples. In some instances, defibrillation segments 28a and 28b may be approximately the same length or, alternatively, different lengths.

The defibrillation electrode segments 28a and 28b may be electrically connected to one or more conductors, which may be disposed in the body wall of lead body 12 or may alternatively be disposed in one or more insulated lumens (not shown) defined by lead body 12. In an example configuration, each of the defibrillation electrode segments 28a and 28b is connected to a common conductor such that a voltage may be applied simultaneously to all the defibrillation electrode segments 28a and 28b to deliver a defibrillation shock to a patient's heart. In other configurations, the defibrillation electrode segments 28a and 28b may be attached to separate conductors such that each defibrillation electrode segment 28a or 28b may apply a voltage independent of the other defibrillation electrode segments 28a or 28b. In this case, ICD 9 or lead 10 may include one or more switches or other mechanisms to electrically connect the defibrillation electrode segments together to function as a common polarity electrode such that a voltage may be applied simultaneously to all the defibrillation electrode segments 28a and 28b in addition to being able to independently apply a voltage.

In one example, the distance between the closest defibrillation electrode segment 28a and 28b and electrodes 32a and 32b is greater than or equal to 2 mm and less than or equal to 1.5 cm. In another example, electrodes 32a and 32b may be spaced apart from the closest one of defibrillation electrode segments 28a and 28b by greater than or equal to 5 mm and less than or equal to 1 cm. In a further example, electrodes 32a and 32b may be spaced apart from the closest one of defibrillation electrode segments 28a and 28b by greater than or equal to 6 mm and less than or equal to 8 mm.

The electrodes 32a and 32b may be configured to deliver low-voltage electrical pulses to the heart or may sense a cardiac electrical activity, e.g., depolarization and repolarization of the heart. As such, electrodes 32a and 32b may be referred to herein as pace/sense electrodes 32a and 32b. In one configuration, electrodes 32a and 32b are ring electrodes. However, in other configurations the electrodes 32a and 32b may be any of a number of different types of electrodes, including ring electrodes, short coil electrodes, paddle electrodes, hemispherical electrodes, directional electrodes, or the like. Electrodes 32a and 32b may be the same or different types of electrodes. Electrodes 32a and 32b may be electrically isolated from an adjacent defibrillation segment 28a or 28b by including an electrically insulating layer of material between electrodes 32a and 32b and the adjacent defibrillation segments 28a and 28b. Each electrode 32a or 32b may have its own separate conductor such that a voltage may be applied to each electrode independently from another electrode 32a or 32b in distal portion 24. In other configurations, each electrode 32a or 32b may be coupled to a common conductor such that each electrode 32a or 32b may apply a voltage simultaneously.

Proximal end 14 of lead body 12 may include one or more connectors 34 to electrically couple lead 10 to the implantable cardioverter-defibrillator (ICD) 9 subcutaneously implanted within the patient, for example, under the left armpit of the patient. The ICD 9 may include a housing 38 that forms a hermetic seal which protects the components of ICD 9. The housing of ICD 9 may be formed of a conductive material, such as titanium or titanium alloy, which may function as a housing electrode for a particular therapy vector between the housing and distal portion 24. ICD 9 may also include a connector assembly that includes electrical feedthroughs through which electrical connections are made between the one or more connectors 34 of lead 10 and the electronic components included within the housing. The housing of ICD 9 may house one or more processors, memories, transmitters, receivers, sensors, sensing circuitry, therapy circuitry, power sources (capacitors and batteries) and/or other appropriate components. The components of ICD 9 may generate and deliver electrical stimulation therapy such as anti tachycardia pacing.

The inclusion of electrodes 32a and 32b between defibrillation electrode segments 28a and 28b provides a number of therapy vectors for the delivery of electrical stimulation therapy to the heart. For example, as shown in FIGS. 1A-1C, at least a portion of the defibrillation electrode 26 and one of the electrodes 32a and 32b may be disposed over the right ventricle, or any chamber of the heart, such that pacing pulses and defibrillation shocks may be delivered to the heart. The housing of ICD 9 may be charged with or function as a polarity different than the polarity of the one or more defibrillation electrode segments 28a and 28b and/or electrodes 32a and 32b such that electrical energy may be delivered between the housing and the defibrillation electrode segment(s) 28a and 28b and/or electrode(s) 32a and 32b to the heart. Each defibrillation electrode segment 28a or 28b may have the same polarity as every other defibrillation electrode segment 28a or 28b when a voltage is applied to it such that a defibrillation shock may be delivered from the entirety of the defibrillation electrode 28. In examples in which defibrillation electrode segments 28a and 28b are electrically connected to a common conductor within lead body 12, this is the only configuration of defibrillation electrode segments 28a and 28b. However, in other examples, defibrillation electrode segments 28a and 28b may be coupled to separate conductors within lead body 12 and may therefore each have different polarities such that electrical energy may flow between defibrillation electrode segments 28a and 28b (or between one of defibrillation electrode segments 28a and 28b and one or more pace/sense electrodes 32a and 32b or the housing electrode) to provide pacing therapy and/or to sense cardiac depolarizations. In this case, the defibrillation electrode segments 28a and 28b may still be electrically coupled together (e.g., via one or more switches within ICD 9) to have the same polarity to deliver a defibrillation shock from the entirety of the defibrillation electrode 28.

Additionally, each electrode 32a and 32b may be configured to conduct electrical pulses directly to the heart, or sense a cardiac depolarization between adjacent defibrillation electrode segments 28a and 28b, whether disposed on the same defibrillation electrode segment 28a or 28b or on other defibrillation electrode segment 28a or 28b, and/or between proximate electrodes 32a and 32b. Additionally electrodes 32a and 32b may conduct electrical pulses between one another, e.g., between one of electrodes 32a and 32b and an inferior and superior electrode 32a and 32b, between one of electrodes 32a and 32b and the housing electrode, or between a plurality of electrodes 32a and 32b (at the same polarity) and the housing electrode at the opposite polarity. As such, each electrode 32a or 32b may have the same polarity as every other electrode 32a or 32b or alternatively, may have different polarities such that different therapy vectors can be utilized to deliver pacing pulses to the heart.

IPD 16 may be implanted within a heart 26 of patient 14. In the example of FIGS. 1A-1C, IPD 16 is implanted within right ventricle of heart 26 to sense electrical activity of heart 26 and deliver pacing therapy, e.g., anti-tachycardia pacing (ATP) therapy, to heart 26. IPD 16 may be attached to an interior wall of the right ventricle of heart 26 via one or more fixation elements that penetrate the tissue. These fixation elements may secure IPD 16 to the cardiac tissue and retain an electrode (e.g., a cathode or an anode) in contact with the cardiac tissue. However, in other examples, system 8 may include additional pacing devices 16 within respective chambers of heart 26 (e.g., right or left atrium and/or left ventricle). In further examples, a cardiac pacing device configured similarly to IPD 16 may be attached to an external surface of heart 26 (e.g., in contact with the epicardium) such that the pacing device is disposed outside of heart 26.

IPD 16 may be capable sensing electrical signals using the electrodes carried on the housing of IPD 16. These electrical signals may be electrical signals generated by cardiac muscle and indicative of depolarizations and repolarizations of heart 26 at various times during the cardiac cycle. IPD 16 may analyze the sensed electrical signals to detect tachyarrhythmias, such as ventricular tachycardia or ventricular fibrillation. In response to detecting the tachyarrhythmia, IPD 16 may, e.g., depending on the type of tachyarrhythmia, begin to deliver ATP therapy via the electrodes of IPD 16.

In some examples, IPD 16 and ICD 9 may be may be configured to communicate with one another, e.g., via radio-frequency communication, to cooperate with one another. For example, IPD 16 and ICD 9 may communicate information, such as sense signals and/or delivered signals, and may coordinate to establish pacing and/or sensing vectors between respective electrodes on ICD 9, IPD 16, and/or lead 10. IPD 16 and ICD 9 may be configured for one-way or two-way communication.

In other examples, IPD 16 and ICD 9 are not configured to communicate with each other. In such examples, each of IPD 16 and ICD 9 may independently monitor the electrical activity of heart, and deliver therapy in response to detecting arrhythmia. In such examples, one or both of IPD 16 and ICD 9 may be configured to detect activity of, e.g., delivery of therapy by, the other. In this manner, delivery of therapies by IPD 16 and ICD 9 may be coordinated without conventional uni- or bi-directional communication between the devices.

Although FIGS. 1A-1C are described in the context of an ICD 9 connected to lead 10 and IPD 16, the techniques may be applicable to other coexistent systems. For example, a medical device that includes a lead having a distal portion that is implanted above the sternum (or other extra-thoracic, subcutaneous location) instead of being implanted below the ribs and/or sternum. As another example, instead of an intracardiac pacing device, a pacing system may be implanted having a subcutaneous or submuscular pacemaker and one or more leads connected to and extending from the pacemaker into one or more chambers of the heart or attached to the outside of the heart to provide pacing therapy to the one or more chambers. As such, the example of FIGS. 1A-1C is illustrated for exemplary purposes only and should not be considered limiting of the techniques described herein.

External device 21 may be configured to communicate with one or both of ICD 9 and IPD 16. In examples where external device 21 only communicates with one of subcutaneous ICD 9 and IPD 16, the non-communicative device may receive instructions from or transmit data to the device in communication with external device 21. In some examples, external device 21 comprises a handheld computing device, computer workstation, or networked computing device. External device 21 may include a user interface that receives input from a user. In other examples, the user may also interact with external device 21 remotely via a networked computing device. The user may interact with external device 21 to communicate with IPD 16 and/or ICD 9. For example, the user may interact with external device 21 to send an interrogation request and retrieve therapy delivery data, update therapy parameters that define therapy, manage communication between IPD 16 and/or ICD 9, or perform any other activities with respect to IPD 16 and/or ICD 9. Although the user is a physician, technician, surgeon, electrophysiologist, or other healthcare professional, the user may be patient 14 in some examples.

External device 21 may also allow the user to define how IPD 16 and/or ICD 9 senses electrical signals (e.g., ECGs), detects arrhythmias such as tachyarrhythmias, delivers therapy, and communicates with other devices of system 8. For example, external device 21 may be used to change tachyarrhythmia detection parameters. In another example, external device 21 may be used to manage therapy parameters that define therapies such as ATP therapy. Moreover, external device 21 may be used to alter communication protocols between IPD 16 and ICD 9. For example, external device 21 may instruct IPD 16 and/or ICD 9 to switch between one-way and two-way communication and/or change which of IPD 16 and/or ICD 9 are tasked with initial detection of arrhythmias.

External device 21 may communicate with IPD 16 and/or ICD 9 via wireless communication using any techniques known in the art. Examples of communication techniques may include, for example, proprietary and non-proprietary radiofrequency (RF) telemetry, but other techniques are also contemplated. In some examples, external device 21 may include a programming head that may be placed proximate to patient 14's body near the IPD 16 and/or ICD 9 implant site in order to improve the quality or security of communication between IPD 16 and/or ICD 9 and external device 21.

In some examples, IPD 16 and ICD 9 may engage in communication to facilitate the appropriate detection of arrhythmias and/or delivery of anti-tachycardia therapy. Anti-tachycardia therapy may include anti-tachycardia pacing (ATP). The communication may include one-way communication in which one device is configured to transmit communication messages and the other device is configured to receive those messages. The communication may instead include two-way communication in which each device is configured to transmit and receive communication messages. Although the examples below describe detection of tachyarrhythmias and the delivery of ATP, IPD 16 and ICD 9 may be configured to communicate with each other and provide alternative electrical stimulation therapies. Two-way communication and coordination of the delivery of patient therapies between IPD 16 and ICD 9 is described in commonly-assigned U.S. Pat. No. 8,744,572 to Greenhut et al., titled, "SYSTEMS AND METHODS FOR LEADLESS PACING AND SHOCK THERAPY," and issued Jun. 3, 2014, the entire content of which is incorporated by reference herein.

The leads and systems described herein may be used at least partially within the substernal space, e.g., within anterior mediastinum of patient, to provide a medical device system. An implanter (e.g., physician) may implant the distal portion of the lead intrathoracically using any of a number of implant tools, e.g., tunneling rod, sheath, or other tool that can traverse the diagrammatic attachments and form a tunnel in the substernal location. For example, the implanter may create an incision near the center of the torso of the patient, e.g., and introduce the implant tool into the substernal location via the incision. The implant tool is advanced from the incision superior along the posterior of the sternum in the substernal location. The distal end of lead 10 is introduced into tunnel via implant tool (e.g., via a sheath). As the distal end of lead 10 is advanced through the substernal tunnel, the distal end of lead 10 is relatively straight. The preformed or shaped undulating portion is flexible enough to be straightened out while routing the lead 10 through a sheath or other lumen or channel of the implant tool. Once the distal end of lead 10 is in place, the implant tool is withdrawn toward the incision and removed from the body of the patient while leaving lead 10 in place along the substernal path. As the implant tool is withdrawn, the distal end of lead 10 takes on its pre-formed undulating configuration. Thus, as the implant tool is withdrawn, the undulating configuration pushes electrodes 32a and 32b toward the left side of sternum compared to electrode segments 28a and 28b. As mentioned above, the implanter may align the electrodes 32a and 32b along the anterior median line (or midsternal line) or the left sternal lines (or left lateral sternal line).

Although system 8 is illustrated as including both extracardiovascular ICD system 6 and IPD 16, in some examples, a system may include extracardiovascular ICD system 6 without IPD 16. In such examples, ICD system 6 may perform the methods described herein without the use of IPD 6. In some examples, system 8 may include extracardiovascular ICD system 6 and IPD 16 and extracardiovascular ICD system 6 may, at some times, perform the methods described herein in coordination with IPD 16 and, at other times, perform the methods described herein without the use of IPD 16.

Figure 2:
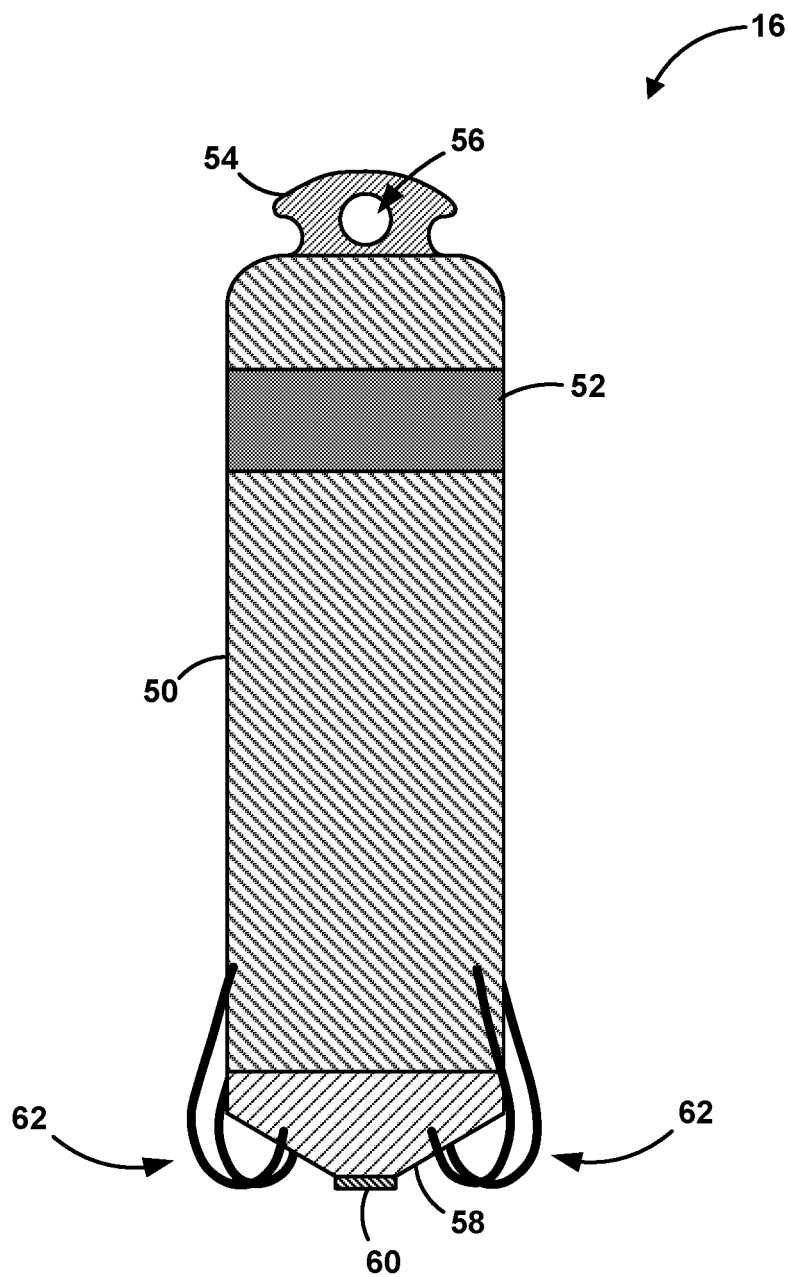
FIG. 2 is a conceptual drawing illustrating an example configuration of the intracardiovascular pacing device (IPD) of the implantable medical device system of FIGS. 1A-1C.

FIG. 2 is a conceptual drawing illustrating an example configuration of IPD 16 of the medical device system of FIGS. 1A-1C. As shown in FIG. 2, IPD 16 includes case 50, cap 58, electrode 60, electrode 52, fixation mechanisms 62, flange 54, and opening 56. Together, case 50 and cap 58 may be considered the housing of IPD 16. In this manner, case 50 and cap 58 may enclose and protect the various electrical components within IPD 16. Case 50 may enclose substantially all of the electrical components, and cap 58 may seal case 50 and create the hermetically sealed housing of IPD 16. Although IPD 16 is generally described as including one or more electrodes, IPD 16 may typically include at least two electrodes (e.g., electrodes 52 and 60) to deliver an electrical signal (e.g., therapy such as ATP) and/or provide at least one sensing vector.

Electrodes 52 and 60 are carried on the housing created by case 50 and cap 58. In this manner, electrodes 52 and 60 may be considered leadless electrodes. In the example of FIG. 2, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode and electrode 52 may be used as an anode, or vice versa, for delivering pacing stimulation therapy such as ATP. However, electrodes 52 and 60 may be used in any stimulation configuration. In addition, electrodes 52 and 60 may be used to detect intrinsic electrical signals from cardiac muscle. In other examples, IPD 16 may include three or more electrodes, where each electrode may deliver therapy and/or detect intrinsic signals. ATP delivered by IPD 16, as compared with alternative devices, may be considered to be "painless" to patient 14 or even undetectable by patient 14 since the electrical stimulation occurs very close to or at cardiac muscle and at relatively low energy levels.

Fixation mechanisms 62 may attach IPD 16 to cardiac tissue. Fixation mechanisms 62 may be active fixation tines, screws, clamps, adhesive members, or any other types of attaching a device to tissue. As shown in the example of FIG. 2, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of IPD 16. For example, a suture or other device may be inserted around flange 54 and/or through opening 56 and attached to tissue. In this manner, flange 54 may provide a secondary attachment structure to tether or retain IPD 16 within heart 18 if fixation mechanisms 62 fail. Flange 54 and/or opening 56 may also be used to extract IPD 16 once the IPD needs to be explanted (or removed) from patient 14 if such action is deemed necessary.

The techniques described herein are generally described with regard to a leadless pacing device such as IPD 16. IPD 16 may be an example of an anti-tachycardia pacing device (ATPD). However, alternative implantable medical devices may be used to perform the same or similar functions as IPD 16, e.g., delivering ATP to heart 26 and, in some examples, communicate with ICD 9. In some examples, IPD 16 may include one or more relatively short leads configured to place one or more respective additional electrodes at another location within the same chamber of the heart or a different chamber of the heart. In this manner, the housing of the ATPD may not carry all of the electrodes used to deliver ATP or perform other functions. In other examples, each electrode of IPD 16 may be carried by one or more leads (e.g., the housing of IPD 16 may not carry any of the electrodes). In some examples, system 8 may exclude IPD 16 or IPD 16 may not be able to deliver pacing (e.g. due to expiration or power source or malfunction) and ICD 9 may instead deliver pacing to heart 26. In other examples, both IPD 16 and ICD 9 may deliver pacing.

In another example, the ATPD may be configured to be implanted external to heart 26, e.g., near or attached to the epicardium of heart 26. An electrode carried by the housing of the ATPD may be placed in contact with the epicardium and/or one or more electrodes of leads coupled to the ATPD may be placed in contact with the epicardium at locations sufficient to provide therapy such as ATP (e.g., on external surfaces of the left and/or right ventricles). In any example, subcutaneous ICD 9 may communicate with one or more leadless or leaded devices implanted internal or external to heart 26.

Figure 3:
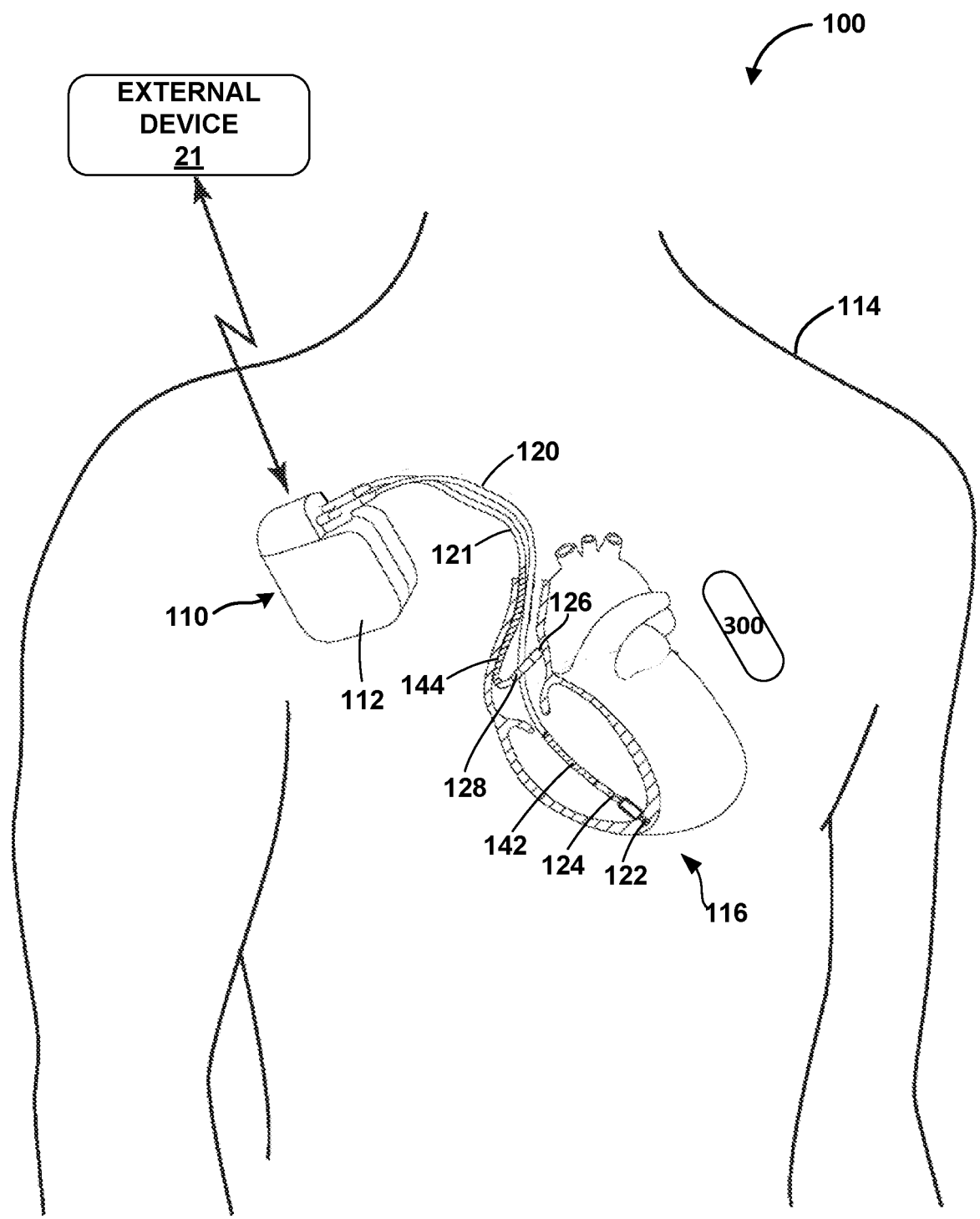
FIG. 3 is a schematic diagram of another example implantable medical device system in conjunction with a patient.

FIG. 3 is a schematic diagram of another example implantable medical device system 100 in conjunction with a patient 114. As illustrated in FIG. 3, a medical device system 100 for sensing cardiac events (e.g. P-waves and R-waves) and detecting tachyarrhythmia episodes may include PCD 110, ventricular lead 120, atrial lead 121, and insertable cardiac monitor (ICM) 300. In one example, PCD 110 may be embodied as an implantable cardioverter-defibrillator (ICD) capable of delivering pacing, cardioversion and defibrillation therapy to the heart 116 of a patient 114. Ventricular lead 120 and atrial lead 121 are electrically coupled to PCD 110 and extend into the patient's heart 116 via a vein. Ventricular lead 20 includes electrodes 122 and 124 shown positioned on the lead in the patient's right ventricle (RV) for sensing ventricular EGM signals and pacing in the RV. Atrial lead 121 includes electrodes 126 and 128 positioned on the lead in the patient's right atrium (RA) for sensing atrial EGM signals and pacing in the RA.

Ventricular lead 120 additionally carries high voltage coil electrodes 142 and 144 used to deliver cardioversion and defibrillation shock pulses. Both the ventricular lead 120 and the atrial lead 121 may be used to acquire intracardiac EGM signals from the patient 114 and to deliver therapy in response to the acquired data. PCD 110 is shown as a dual chamber ICD, but in some examples, system 100 may be embodied as a multi-chamber system including a coronary sinus lead extending into the right atrium, through the coronary sinus and into a cardiac vein to position electrodes along the left ventricle (LV) for sensing LV EGM signals and delivering pacing pulses to the LV.

Implantable medical device circuitry configured for performing the functions of PCD 110 described herein and associated battery or batteries are housed within a sealed housing 112. Housing 112 may be conductive so as to serve as an electrode for use as an indifferent electrode during pacing or sensing or as an active electrode during defibrillation. As such, housing 112 is also referred to herein as "housing electrode" 12.

ICM 300 may be a device for sensing extracardiac ECG signals. ICM 300 may be implanted within patient 14 and may communicate with PCD 110 and/or external device 21. ICM 300 may include a plurality of electrodes for sensing ECG signals. ICM 300 will be described in further detail below with reference to FIG. 4.

EGM signal data acquired by PCD 110 can be transmitted to an external device 21. External device 21 may be embodied as a programmer, e.g. used in a clinic or hospital to communicate with PCD 110 via wireless telemetry. External device 21 may be coupled to a remote patient monitoring system, such as Carelink®, available from Medtronic, Inc., Minneapolis, Minn. External device 21 is used to program commands or operating parameters into PCD 110 for controlling IMD function and to interrogate PCD 110 to retrieve data, including device operational data as well as physiological data accumulated in IMD memory. Examples of communication techniques used by PCD 110 and external device 21 include low frequency or radiofrequency (RF) telemetry, which may be an RF link established via Bluetooth, WiFi, or MICS.

External device 21 may be configured to communicate with one or both of PCD 110 and ICM 300. In examples where external device 21 only communicates with one of PCD 110 and ICM 300, the non-communicative device may receive instructions from or transmit data to the device in communication with external device 21. In some examples, external device 21 comprises a handheld computing device, computer workstation, or networked computing device. External device 21 may include a user interface that receives input from a user. In other examples, the user may also interact with external device 21 remotely via a networked computing device. The user may interact with external device 21 to communicate with PCD 110 and/or ICM 300. For example, the user may interact with external device 21 to send an interrogation request and retrieve therapy delivery data, update therapy parameters that define therapy, manage communication between PCD 110 and/or ICM 300, or perform any other activities with respect to PCD 110 and/or ICM 300. Although the user is a physician, technician, surgeon, electrophysiologist, or other healthcare professional, the user may be patient 14 in some examples.

External device 21 may also allow the user to define how PCD 110 and/or ICM 300 senses electrical signals (e.g., ECGs), detects arrhythmias such as tachyarrhythmias, delivers therapy, and communicates with other devices of system 100. For example, external device 21 may be used to change tachyarrhythmia detection parameters. In another example, external device 21 may be used to manage therapy parameters that define therapies such as ATP therapy. Moreover, external device 21 may be used to alter communication protocols between PCD 110 and ICM 300.

External device 21 may communicate with PCD 110 and/or ICM 300 via wireless communication using any techniques known in the art. Examples of communication techniques are described above with reference to FIG. 1A. In some examples, external device 21 may include a programming head that may be placed proximate to patient 14's body near the PCD 110 and/or ICM 300 implant site in order to improve the quality or security of communication between PCD 110 and/or ICM 300 and external device 21.

In some examples, PCD 110 and ICM 300 may engage in communication to facilitate the appropriate detection of arrhythmias and/or delivery of anti-tachyarrhythmia therapy. Anti-arrhythmia therapy may include anti-tachycardia pacing (ATP). The communication may include one-way communication in which one device is configured to transmit communication messages and the other device is configured to receive those messages. The communication may instead include two-way communication in which each device is configured to transmit and receive communication messages. Although the examples below describe detection of tachyarrhythmias and the delivery of ATP, PCD 110 and ICM 300 may be configured to communicate with each other and provide alternative electrical stimulation therapies.

In some examples, system 100 may exclude ICM 300 and PCD 110 may deliver ATP therapy, sense evoked responses, and/or modify the ATP therapy based on the sensed evoked responses independently and/or in coordination with external device 21. In such an example, PCD 100 may use a plurality of pacing vectors to deliver ATP therapy to different locations in the heart without the need of ICM 300.

Figure 4:
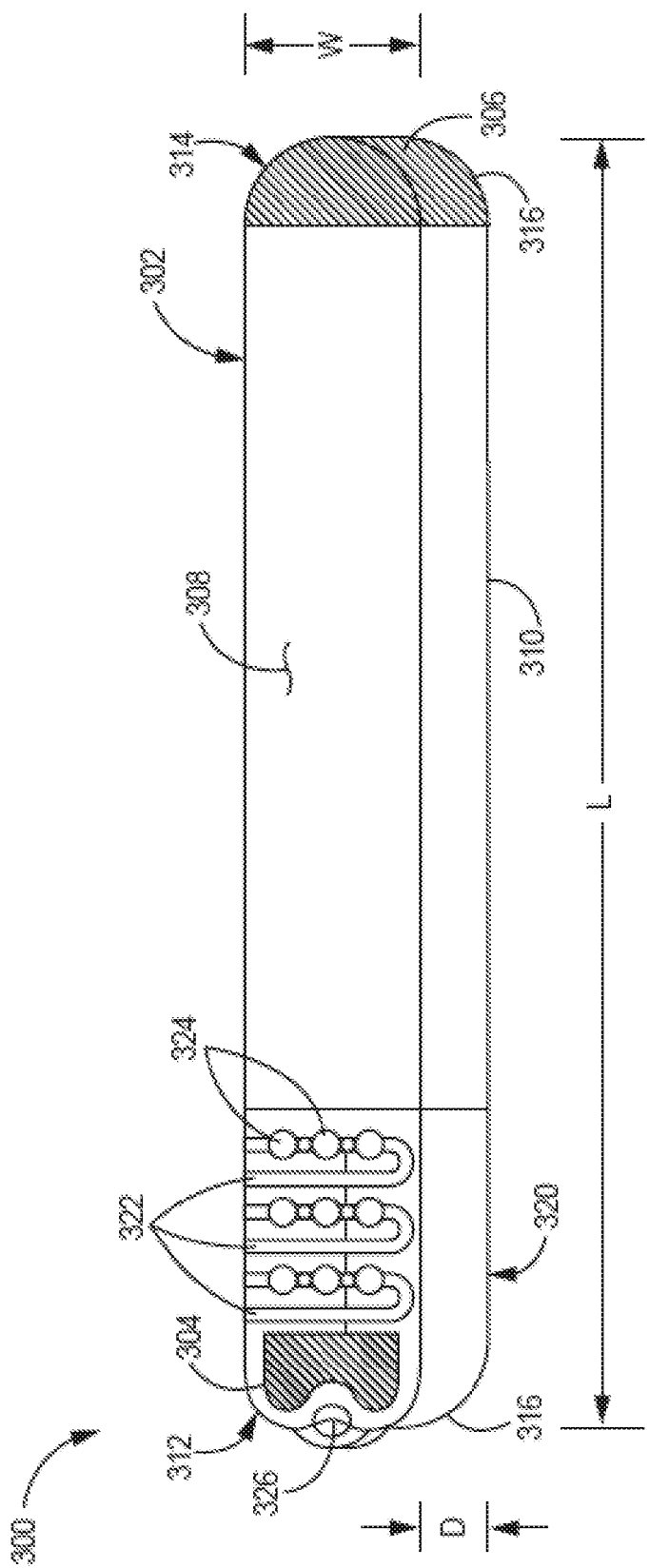
FIG. 4 is a conceptual drawing illustrating an example configuration of the insertable cardiac monitor (ICM) of the implantable medical device system of FIG. 3.

FIG. 4 is a conceptual drawing illustrating an example configuration of the insertable cardiac monitor (ICM) 300 of implantable medical device system 100 of FIG. 3. In the example shown in FIG. 4, ICM 300 may be embodied as a monitoring device having housing 302, proximal electrode 304 and distal electrode 306. Housing 302 may further comprise first major surface 308, second major surface 310, proximal end 312, and distal end 314. Housing 302 encloses electronic circuitry and a power source (shown in FIG. 9) located inside the ICM 300 and protects the circuitry contained therein from body fluids. Electrical feedthroughs provide electrical connection of electrodes 304 and 306.

In the example shown in FIG. 4, ICM 300 is defined by a length L, a width W and thickness or depth D and is in the form of an elongated rectangular prism wherein the length L is much larger than the width W, which in turn is larger than the depth D. In one example, the geometry of the ICM 300—in particular a width W greater than the depth D—is selected to allow ICM 300 to be inserted under the skin of the patient using a minimally invasive procedure and to remain in the desired orientation during insertion. For example, the device shown in FIG. 4 includes radial asymmetries (notably, the rectangular shape) along the longitudinal axis that maintains the device in the proper orientation following insertion. For example, in one example the spacing between proximal electrode 304 and distal electrode 306 may range from 30 millimeters (mm) to 55 mm, 35 mm to 55 mm, and from 40 mm to 55 mm and may be any range or individual spacing from 25 mm to 60 mm. In addition, ICM 300 may have a length L that ranges from 30 mm to about 70 mm. In other examples, the length L may range from 40 mm to 60 mm, 45 mm to 60 mm and may be any length or range of lengths between about 30 mm and about 70 mm. In addition, the width W of major surface 308 may range from 3 mm to 10 mm and may be any single or range of widths between 3 mm and 10 mm. The thickness of depth D of ICM 300 may range from 2 mm to 9 mm. In other examples, the depth D of ICM 300 may range from 2 mm to 5 mm and may be any single or range of depths from 2 mm to 9 mm. In addition, ICM 300 according to an example of the present disclosure is has a geometry and size designed for ease of implant and patient comfort. Examples of ICM 300 described in this disclosure may have a volume of three cubic centimeters (cm) or less, 1.5 cubic cm or less or any volume between three and 1.5 cubic centimeters.

In the example shown in FIG. 4, once inserted within the patient, the first major surface 308 faces outward, toward the skin of the patient while the second major surface 310 is located opposite the first major surface 308. In addition, in the example shown in FIG. 4, proximal end 312 and distal end 314 are rounded to reduce discomfort and irritation to surrounding tissue once inserted under the skin of the patient. ICM 300, including instrument and method for inserting ICM 300 is described, for example, in U.S. Patent Publication No. 2014/0276928, incorporated herein by reference in its entirety.

Proximal electrode 304 and distal electrode 306 are used to sense cardiac signals, e.g. ECG signals, intra-thoracically or extra-thoracically, which may be sub-muscularly or subcutaneously. ECG signals may be stored in a memory of the ICM 300, and ECG data may be transmitted via integrated antenna 322 to another medical device, which may be another implantable device or an external device, such as PCD 110 or external device 21. In some example, electrodes 304 and 306 may additionally or alternatively be used for sensing any bio-potential signal of interest, which may be, for example, an EGM, EEG, EMG, or a nerve signal, from any implanted location.

In the example shown in FIG. 4, proximal electrode 304 is in close proximity to the proximal end 312 and distal electrode 306 is in close proximity to distal end 314. In this example, distal electrode 306 is not limited to a flattened, outward facing surface, but may extend from first major surface 308 around rounded edges 316 and/or end surface 318 and onto the second major surface 310 so that the electrode 306 has a three-dimensional curved configuration. In the example shown in FIG. 4, proximal electrode 304 is located on first major surface 308 and is substantially flat, outward facing. However, in other examples proximal electrode 304 may utilize the three dimensional curved configuration of distal electrode 306, providing a three dimensional proximal electrode (not shown in this example). Similarly, in other examples distal electrode 306 may utilize a substantially flat, outward facing electrode located on first major surface 308 similar to that shown with respect to proximal electrode 304. The various electrode configurations allow for configurations in which proximal electrode 304 and distal electrode 306 are located on both first major surface 308 and second major surface 310. In other configurations, such as that shown in FIG. 4, only one of proximal electrode 304 and distal electrode 306 is located on both major surfaces 308 and 310, and in still other configurations both proximal electrode 304 and distal electrode 306 are located on one of the first major surface 308 or the second major surface 310 (i.e., proximal electrode 304 located on first major surface 308 while distal electrode 306 is located on second major surface 310). In another example, ICM 300 may include electrodes on both major surface 308 and 310 at or near the proximal and distal ends of the device, such that a total of four electrodes are included on ICM 300. Electrodes 304 and 306 may be formed of a plurality of different types of biocompatible conductive material, e.g. stainless steel, titanium, platinum, iridium, or alloys thereof, and may utilize one or more coatings such as titanium nitride or fractal titanium nitride.

In the example shown in FIG. 4, proximal end 312 includes a header assembly 320 that includes one or more of proximal electrode 304, integrated antenna 322, anti-migration projections 324, and/or suture hole 326. Integrated antenna 322 is located on the same major surface (i.e., first major surface 308) as proximal electrode 304 and is also included as part of header assembly 320. Integrated antenna 322 allows ICM 300 to transmit and/or receive data. In other examples, integrated antenna 322 may be formed on the opposite major surface as proximal electrode 304, or may be incorporated within the housing 322 of ICM 300. In the example shown in FIG. 4, anti-migration projections 324 are located adjacent to integrated antenna 322 and protrude away from first major surface 308 to prevent longitudinal movement of the device. In the example shown in FIG. 4, anti-migration projections 324 includes a plurality (e.g., nine) small bumps or protrusions extending away from first major surface 308. As discussed above, in other examples anti-migration projections 324 may be located on the opposite major surface as proximal electrode 304 and/or integrated antenna 322. In addition, in the example shown in FIG. 4 header assembly 320 includes suture hole 326, which provides another means of securing ICM 300 to the patient to prevent movement following insert. In the example shown, suture hole 326 is located adjacent to proximal electrode 304. In one example, header assembly 320 is a molded header assembly made from a polymeric or plastic material, which may be integrated or separable from the main portion of ICM 300.

According to the techniques of this disclosure, one or more devices may deliver ATP therapy, sense evoked response(s) of the heart to the delivered ATP therapy, determine latency metric(s) of the evoked response(s), and modify the ATP therapy based on the latency metric(s). The modification may be to a current pulse train of the ATP therapy and/or a subsequent pulse train of the ATP therapy. The latency metric(s) may be local, meaning the latency metric(s) may be based on evoked response(s) sensed at or near a location where the ATP therapy has been delivered, and/or the latency metric(s) may be global, meaning the latency metric(s) may be based on evoked response(s) sensed further away from the location where the ATP therapy has been delivered or through analysis of a global activation time indicator such as the duration from stimulation delivery to the end of the QRS portion of the evoked response. Any of IPD 16, ICD 9, and PCD 110 may be a device that delivers and modifies ATP therapy based on a determined latency metric. If IPD 16 delivers the ATP therapy, ICD 9 may sense evoked response(s) at a different location to be used to determine a global latency metric. If PCD 110 delivers the ATP therapy, ICM 300 may sense evoked response(s) at a different location to be used to determine a global latency metric. Example configurations of these devices, including how they function to perform these tasks, are discussed in further detail below.

Figure 5:
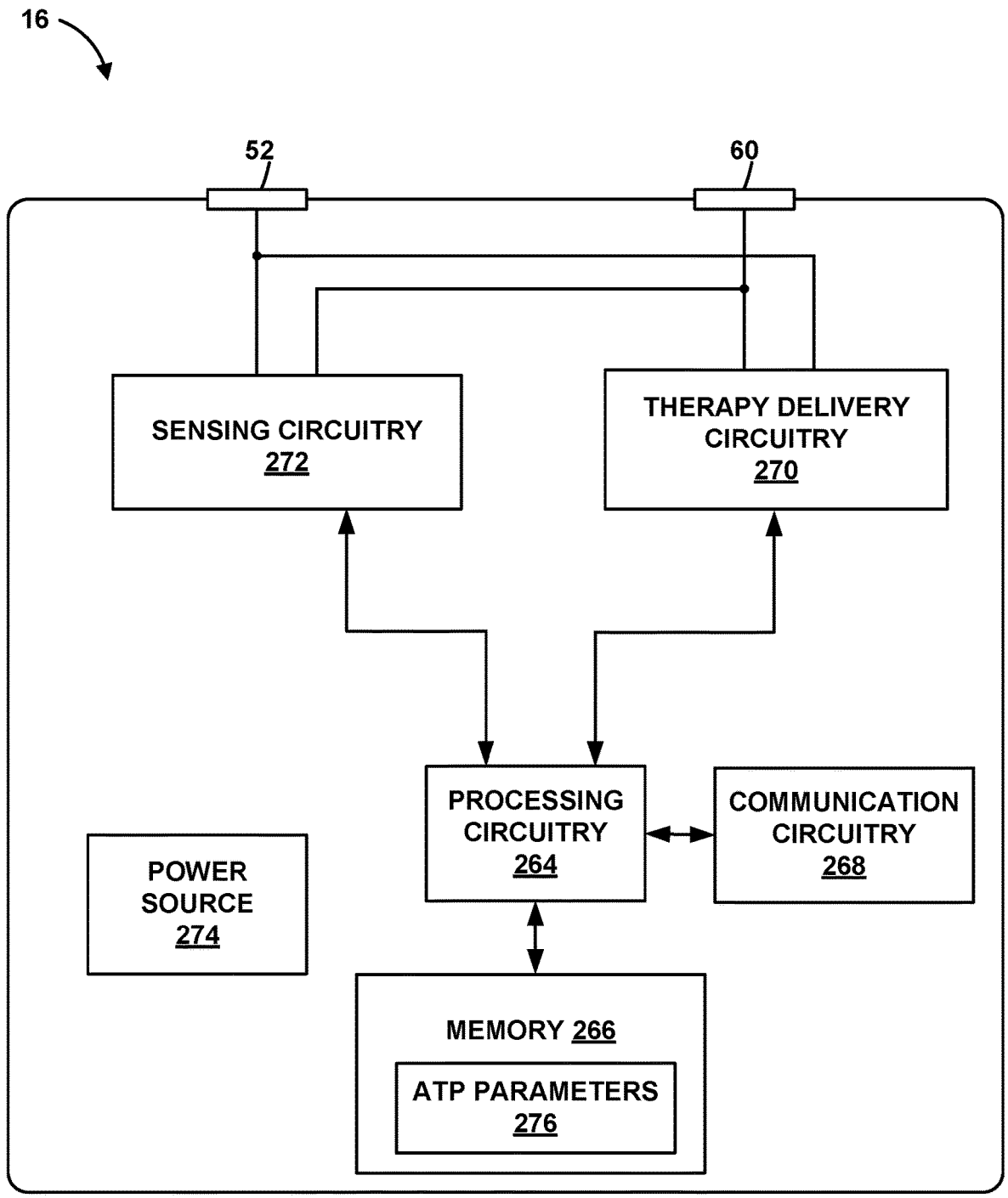
FIG. 5 is a functional block diagram illustrating an example configuration of the IPD of FIGS. 1A-1C and 2.

FIG. 5 is a functional block diagram illustrating an example configuration of IPD 16 of FIGS. 1A-1C and 2. In the illustrated example, IPD 16 includes processing circuitry 264, memory 226, therapy delivery circuitry 270, sensing circuitry 272, communication circuitry 268, and power source 274. The electronic components may receive power from a power source 274, which may be a rechargeable or non-rechargeable battery. In other examples, IPD 16 may include more or fewer electronic components. The described circuitry may be implemented together on a common hardware component or separately as discrete but interoperable hardware or software components. Depiction of different features as circuitry is intended to highlight different functional aspects and does not necessarily imply that such circuitry must be realized by separate hardware or software components. Rather, functionality associated with one or more circuitry may be performed by separate hardware or software components, or integrated within common or separate hardware or software components.

Memory 226 includes computer-readable instructions that, when executed by processing circuitry 264, cause IPD 16 and processing circuitry 264 to perform various functions attributed to IPD 16 and processing circuitry 264 herein (e.g., delivering anti-tachycardia pacing, sensing an evoked response, and/or modifying the ATP therapy). Memory 226 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 264 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 264 may include multiple components, such as any combination of one or more microprocessors, one or more controllers, one or more DSPs, one or more ASICs, or one or more FPGAs, as well as other discrete or integrated logic circuitry. The functions attributed to processing circuitry 264 herein may be embodied as software, firmware, hardware or any combination thereof.

Therapy delivery circuitry 270 is electrically coupled to electrodes 52 and 60 carried on the housing of IPD 16. Therapy delivery circuitry 270 may include one or more pulse generators, capacitors, and/or other components capable of generating and/or storing energy to deliver as pacing therapy. In the illustrated example, therapy delivery circuitry 270 is configured to generate and deliver electrical stimulation therapy to heart 26. For example, therapy delivery circuitry 270 may deliver the electrical stimulation therapy to a portion of cardiac muscle within heart 26 via electrodes 52 and 60. In some examples, therapy delivery circuitry 270 may deliver pacing stimulation, e.g., ATP therapy, in the form of voltage or current electrical pulses. In other examples, therapy delivery circuitry 270 may deliver stimulation in the form of other signals, such as sine waves, square waves, or other substantially continuous time signals.

Processing circuitry 264 controls therapy delivery circuitry 270 to deliver cardiac pacing therapy to heart 26 according to parameters, which may be stored in memory 226. For example, processing circuitry 264 may control therapy delivery circuitry 270 to deliver pacing pulses with the amplitudes, pulse widths, frequency, or electrode polarities specified by the therapy parameters, including intervals that define under what conditions and when pacing pulses should be delivered. In this manner, therapy delivery circuitry 270 may deliver pacing pulses (e.g., ATP pulses) to heart 26 via electrodes 52 and 60. Although IPD 16 may only include two electrodes, e.g., electrodes 52 and 60, IPD 16 may utilize three or more electrodes in other examples. IPD 16 may use any combination of electrodes to deliver therapy and/or detect electrical signals from patient 14.

Processing circuitry 264 may control therapy delivery circuitry 270 to deliver pacing pulses for ATP therapy according to ATP parameters 276 stored in memory 266. ATP therapy parameters 276 may include pulse intervals, pulse width, current and/or voltage amplitudes, and durations for each pacing mode. For example, the pulse interval may be based on a fraction of the detected ventricular tachycardia (VT) cycle length and be between approximately 150 milliseconds and 500 milliseconds (e.g., between approximately 2.0 hertz and 7.0 hertz), and the pulse width may be between approximately 0.5 milliseconds and 2.0 milliseconds. The amplitude of each pacing pulse may be between approximately 2.0 volts and 10.0 volts. In some examples, the pulse amplitude may be approximately 6.0 V and the pulse width may be approximately 1.5 milliseconds; another example may include pulse amplitudes of approximately 5.0 V and pulse widths of approximately 1.0 milliseconds. Each train of pulses during ATP may last for a duration of between approximately 0.5 seconds to approximately 15 seconds or be defined as a specific number of pulses. Each pulse, or burst of pulses, may include a ramp up in amplitude or in pulse rate. In addition, trains of pulses in successive ATP periods may be delivered at increasing pulse rate in an attempt to capture the heart and terminate the tachycardia. Example ATP parameters and other criteria involving the delivery of ATP are described in U.S. Pat. No. 6,892,094 to Ousdigian et al., entitled, "COMBINED ANTI-TACHYCARDIA PACING (ATP) AND HIGH VOLTAGE THERAPY FOR TREATING VENTRICULAR ARRHYTHMIAS," and issued on May 10, 2005, the entire content of which is incorporated herein by reference and U.S. Pat. No. 8,706,221 to Belk et al., entitled, "METHOD AND DEVICE FOR DELIVERING ANTI-TACHYCARDIA PACING THERAPY," and issued on Apr. 22, 2014, the entire content of which is incorporated herein by reference.

Processing circuitry 264 controls therapy delivery circuitry 270 to generate and deliver pacing pulses with any of a number of shapes, amplitudes, pulse widths, or other characteristic to capture the heart. For example, the pacing pulses may be monophasic, biphasic, or multi-phasic (e.g., more than two phases). The pacing thresholds of the heart when delivering pacing pulses may depend upon a number of factors, including location, type, size, orientation, and/or spacing of IPD 16 and/or electrodes 52 and/or 60, physical abnormalities of the heart (e.g., pericardial adhesions or myocardial infarctions), or other factor(s).

In examples in which IPD 16 includes more than two electrodes, therapy delivery circuitry 270 may include a switch and processing circuitry 264 may use the switch to select, e.g., via a data/address bus, which of the available electrodes are used to deliver pacing pulses. The switch may include a switch array, switch matrix, multiplexer, or any other type of switching device suitable to selectively couple stimulation energy to selected electrodes.

Sensing circuitry 272 is electrically connected to and monitors signals from some or all of electrodes 52 and 60 in order to monitor electrical activity of heart 26, impedance, or other electrical phenomenon. Sensing may be done to determine heart rates or heart rate variability, or to detect arrhythmias (e.g., tachyarrhythmias or bradycardia) or other electrical signals. Sensing circuitry 272 may also include a switch to select which of the available electrodes (or electrode polarity) are used to sense the heart activity, depending upon which electrode combination, or electrode vector, is used in the current sensing configuration. In examples with several electrodes, processing circuitry 264 may select the electrodes that function as sense electrodes, i.e., select the sensing configuration, via the switch circuitry within sensing circuitry 272. Sensing circuitry 272 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processing circuitry 264, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processing circuitry 264 may control the functionality of sensing circuitry 272 by providing signals via a data/address bus.

The components of sensing circuitry 272 may be analog components, digital components or a combination thereof. Sensing circuitry 272 may, for example, include one or more sense amplifiers, filters, rectifiers, threshold detectors, analog-to-digital converters (ADCs) or the like. Sensing circuitry 272 may convert the sensed signals to digital form and provide the digital signals to processing circuitry 264 for processing or analysis. For example, sensing circuitry 272 may amplify signals from the sensing electrodes and convert the amplified signals to multi-bit digital signals by an ADC. Sensing circuitry 272 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to processing circuitry 264.

Sensing circuitry 272 and/or processing circuitry 264 may also include circuitry for measuring the capture threshold for the delivery of pacing pulses via electrodes 52 and 60. The capture threshold may indicate the voltage and pulse width necessary to induce depolarization of the surrounding cardiac muscle. For example, processing circuitry 264 may periodically control therapy delivery circuitry 270 to modify the amplitude of pacing pulses delivered to patient 12, and sensing circuitry 272 and/or processing circuitry 264 may detect whether the surrounding cardiac tissue depolarized in response to the pacing pulses, i.e., detected whether there was an evoked response to the pacing pulse. Processing circuitry 264 may determine the capture threshold based on the amplitude where loss of capture occurred. Processing circuitry 264 may also determine one or more latency metrics based on detecting the evoked response to ATP therapy pulses, as described in greater detail below.

Processing circuitry 264 may process the signals from sensing circuitry 272 to monitor electrical activity of the heart of the patient. Processing circuitry 264 may store signals obtained by sensing circuitry 2272 as well as any generated EGM waveforms, marker channel data or other data derived based on the sensed signals in memory 266. Processing circuitry 264 may analyze the EGM waveforms and/or marker channel data to detect cardiac events (e.g., tachycardia). In response to detecting the cardiac event, processing circuitry 264 may control therapy delivery circuitry 270 to deliver the desired therapy to treat the cardiac event, e.g., ATP therapy.

In examples in which IPD 16 includes more than two electrodes, therapy delivery circuitry 270 may include a switch and processing circuitry 264 may use the switch to select, e.g., via a data/address bus, which of the available electrodes are used to deliver pacing pulses. The switch may include a switch array, switch matrix, multiplexer, or any other type of switching device suitable to selectively couple stimulation energy to selected electrodes. Processing circuitry 264 may select the electrodes to function as signal electrodes, or the signal vector, via the switch circuitry within therapy delivery circuitry 270. In some instances, the same switch circuitry may be used by both therapy delivery circuitry 270 and sensing circuitry 272. In other instances, each of sensing circuitry 272 and therapy delivery circuitry 270 may have separate switch circuitry.

Processing circuitry 264 may include a timing and control circuitry, which may be embodied as hardware, firmware, software, or any combination thereof. The timing and control circuitry may comprise a dedicated hardware circuit, such as an ASIC, separate from other processing circuitry 264 components, such as a microprocessor, or a software module executed by a component of processing circuitry 264, which may be a microprocessor or ASIC. The timing and control circuitry may implement programmable counters. If IPD 16 is configured to generate and deliver pacing pulses to heart 26, such counters may control the basic time intervals associated with DDD, VVI, DVI, VDD, AAI, DDI, DDDR, VVIR, DVIR, VDDR, AAIR, DDIR and other modes of pacing. Example IPDs that may deliver pacing using such modes are described in U.S. Pat. No. 8,923,963 to Bonner et al., entitled, "LEADLESS PACEMAKER SYSTEM," and issued on Dec. 30, 2014, or in U.S. patent application Ser. No. 13/665,601 to Bonner et al., entitled, "LEADLESS PACEMAKER SYSTEM," and filed on Oct. 31, 2012. U.S. patent application Ser. No. 13/665,492 to Bonner et al. and U.S. patent application Ser. No. 13/665,601 to Bonner et al. are both incorporated herein by reference in their entireties.

Intervals defined by the timing and control circuitry within processing circuitry 264 may include atrial and ventricular pacing escape intervals, refractory periods during which sensed P-waves and R-waves are ineffective to restart timing of the escape intervals, and the pulse widths of the pacing pulses. As another example, the timing and control circuitry may withhold sensing from one or more channels of sensing circuitry 272 for a time interval during and after delivery of electrical stimulation to heart 26. The durations of these intervals may be determined by processing circuitry 264 in response to stored data in memory 226. The timing and control circuitry of processing circuitry 264 may also determine the amplitude of the cardiac pacing pulses.

Interval counters implemented by the timing and control circuitry of processing circuitry 264 may be reset upon sensing of R-waves and P-waves with detection channels of sensing circuitry 272. In examples in which IPD 16 provides pacing, therapy delivery circuitry 270 may include pacer output circuits that are coupled to electrodes 52 and 60, for example, appropriate for delivery of a bipolar or unipolar pacing pulse to one of the chambers of heart 26. In such examples, processing circuitry 264 may reset the interval counters upon the generation of pacing pulses by therapy delivery circuitry 270, and thereby control the basic timing of cardiac pacing functions, including ATP or post-shock pacing.

The value of the count present in the interval counters when reset by sensed R-waves and P-waves may be used by processing circuitry 264 to measure the durations of R-R intervals, P-P intervals, P-R intervals and R-P intervals, which are measurements that may be stored in memory 266. Processing circuitry 264 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 266 may be configured as a plurality of recirculating buffers, capable of holding series of measured intervals, which may be analyzed by processing circuitry 264 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In one example, processing circuitry 264 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. are incorporated herein by reference in their entireties. However, other arrhythmia detection methodologies, such as those methodologies that utilize timing and morphology of the electrocardiogram, may also be employed by processing circuitry 264 in other examples.

In some examples, processing circuitry 264 may determine that tachyarrhythmia has occurred by identification of shortened R-R (or P-P) interval lengths. Generally, processing circuitry 264 detects tachycardia when the interval length falls below 220 milliseconds and fibrillation when the interval length falls below 180 milliseconds. In other examples, processing circuitry 264 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 266. This interval length may need to be detected for a certain number of consecutive cycles, for a certain percentage of cycles within a running window, or a running average for a certain number of cardiac cycles, as examples. In other examples, additional physiological parameters may be used to detect an arrhythmia. For example, processing circuitry 264 may analyze one or more morphology measurements, impedances, or any other physiological measurements to determine that patient 14 is experiencing a tachyarrhythmia.

In the event that an ATP regimen is desired, timing intervals for controlling the generation of ATP therapies by therapy deliver circuitry 270 may be loaded by processing circuitry 264 into the timing and control circuitry based on ATP parameters 276 to control the operation of the escape interval counters therein and to define refractory periods during which detection of R-waves and P-waves is ineffective to restart the escape interval counters for the ATP. An ATP regimen may be desired if processing circuitry 264 detects an atrial or ventricular tachyarrhythmia based on signals from sensing circuitry 272, and/or receives a command from another device or system, such as ICD 9, as examples.

In addition to detecting and identifying specific types of cardiac rhythms, sensing circuitry 272 may also sample the detected intrinsic signals to generate an electrogram or other time-based indication of cardiac events. Processing circuitry 264 may also be able to coordinate the delivery of pacing pulses from different IPDs implanted in different chambers of heart 26, such as an IPD implanted in atrium and/or an IPD implanted in left ventricle. For example, processing circuitry 264 may identify delivered pulses from other IPDs via sensing circuitry 272 and update pulse timing to accomplish a selected pacing regimen. This detection may be on a pulse-to-pulse or beat-to-beat basis, or on a less frequent basis to make slight modifications to pulse rate over time. In other examples, IPDs may communicate with each other via communication circuitry 268 and/or instructions over a carrier wave (such as a stimulation waveform). In this manner, ATP pacing may be coordinated from multiple IPDs.

IPD 16 may deliver ATP therapy using electrodes 52 and 60 and therapy delivery circuitry 270 and may sense a local evoked response using the electrodes 52 and 60 and sensing circuitry 272 to sense at a location that is at or near the location of the delivery of the ATP therapy. Another device, such as ICD 9 may sense a global evoked response to the ATP pacing delivered by IPD 16 by sensing at a location that is a substantial distance from the location of the delivery of the ATP therapy. In other examples, the same device, using different electrode vectors, may be used to sense both local and global evoked responses to delivered ATP therapy delivered by the device. The evoked responses may be detected via the hardware of sensing circuitry 272 similar to R-wave, e.g., using a sense amplifier to detect amplitude above a threshold shortly after delivery of a pacing pulse, and/or may be by detected by processing circuitry 264 determining a spike by signal processing a digitized version of ECG signals from electrodes 52 and 60.

Memory 266 may be configured to store a variety of operational parameters, therapy parameters, including ATP therapy parameters 276, sensed and detected data, and any other information related to the therapy and treatment of patient 14. In the example of FIG. 5, memory 266 may store sensed ECGs, detected arrhythmias, communications from ICD 9, and therapy parameters that define ATP therapy (ATP therapy parameters 276). In other examples, memory 266 may act as a temporary buffer for storing data until it can be uploaded to ICD 9, another implanted device, or external device 21.

Communication circuitry 268 includes any suitable hardware, firmware, software or any combination thereof for communicating with another device, such as external device 21 (FIGS. 1A-1C and 7), ICD 9 (FIGS. 1A-1C and 6), a clinician programmer, a patient monitoring device, or the like. For example, communication circuitry 284 may include appropriate modulation, demodulation, frequency conversion, filtering, and amplifier components for transmission and reception of data. Under the control of processing circuitry 264, communication circuitry 268 may receive downlink telemetry from and send uplink telemetry to external device 21 with the aid of an antenna, which may be internal and/or external. Processing circuitry 264 may provide the data to be uplinked to external device 21 and the control signals for the telemetry circuit within communication circuitry 268, e.g., via an address/data bus. In some examples, communication circuitry 268 may provide received data to processing circuitry 264 via a multiplexer.

In some examples, IPD 16 may signal external device 21 to further communicate with and pass the alert through a network such as the Medtronic CareLink® Network developed by Medtronic, Inc., of Minneapolis, Minn., or some other network linking patient 14 to a clinician. IPD 16 may spontaneously transmit information to the network or in response to an interrogation request from a user.

Power source 274 may be any type of device that is configured to hold a charge to operate the circuitry of IPD 16. Power source 274 may be provided as a rechargeable or non-rechargeable battery. In other example, power source 274 may incorporate an energy scavenging system that stores electrical energy from movement of IPD 16 within patient 14.

The various circuitry of IPD 16 may include any one or more processors, controllers, digital signal processors (DSPs), application specific integrated circuits (ASICs), field programmable gate arrays (FPGAs), or equivalent discrete or integrated circuitry, including analog circuitry, digital circuitry, or logic circuitry.

According to the techniques of this disclosure, IPD 16 may deliver ATP therapy via therapy delivery circuitry 270, sense evoked response(s) of the heart to the delivered ATP therapy via sensing circuitry 272, determine latency metric(s) of the evoked response(s) via processing circuitry 264, and modify the ATP therapy based on the latency metric(s) via processing circuitry 264. The modification may be to a current pulse train of the ATP therapy and/or a subsequent pulse train of the ATP therapy. Processing circuitry 264 may modify the ATP therapy by modifying ATP parameters 276 stored in memory 266. The latency metric(s) may be local (based on evoked response(s) sensed at or near a location where the ATP therapy has been delivered) and/or the latency metric(s) may be global (based on evoked response(s) sensed further away from the location where the ATP therapy has been delivered). IPD 16 may work in coordination with ICD 9. For example, IPD 16 may deliver ATP therapy and sense evoked response(s) at one or more locations and ICD 9 may deliver ATP therapy and sense evoked response(s) at one or more different locations. In some examples, IPD 16 may deliver ATP therapy and sense evoked response(s) at the same or similar location to determine local latency metric(s) and ICD 9 may sense evoked response(s) to the therapy delivered by IPD 16 to determine global latency metrics. Communication circuitry 268 may allow IPD 16 to communicate with ICD 9 to provide for such coordination. In some examples, ICD 9 may determine latency metric(s) and communicate them to IPD 16. In some examples, ICD 9 may communicate sensed evoked response(s) and communicate them to IPD 16, processing circuitry 264 may determine latency metric(s) based on the evoked response(s) information received from ICD 9.

Figure 6:
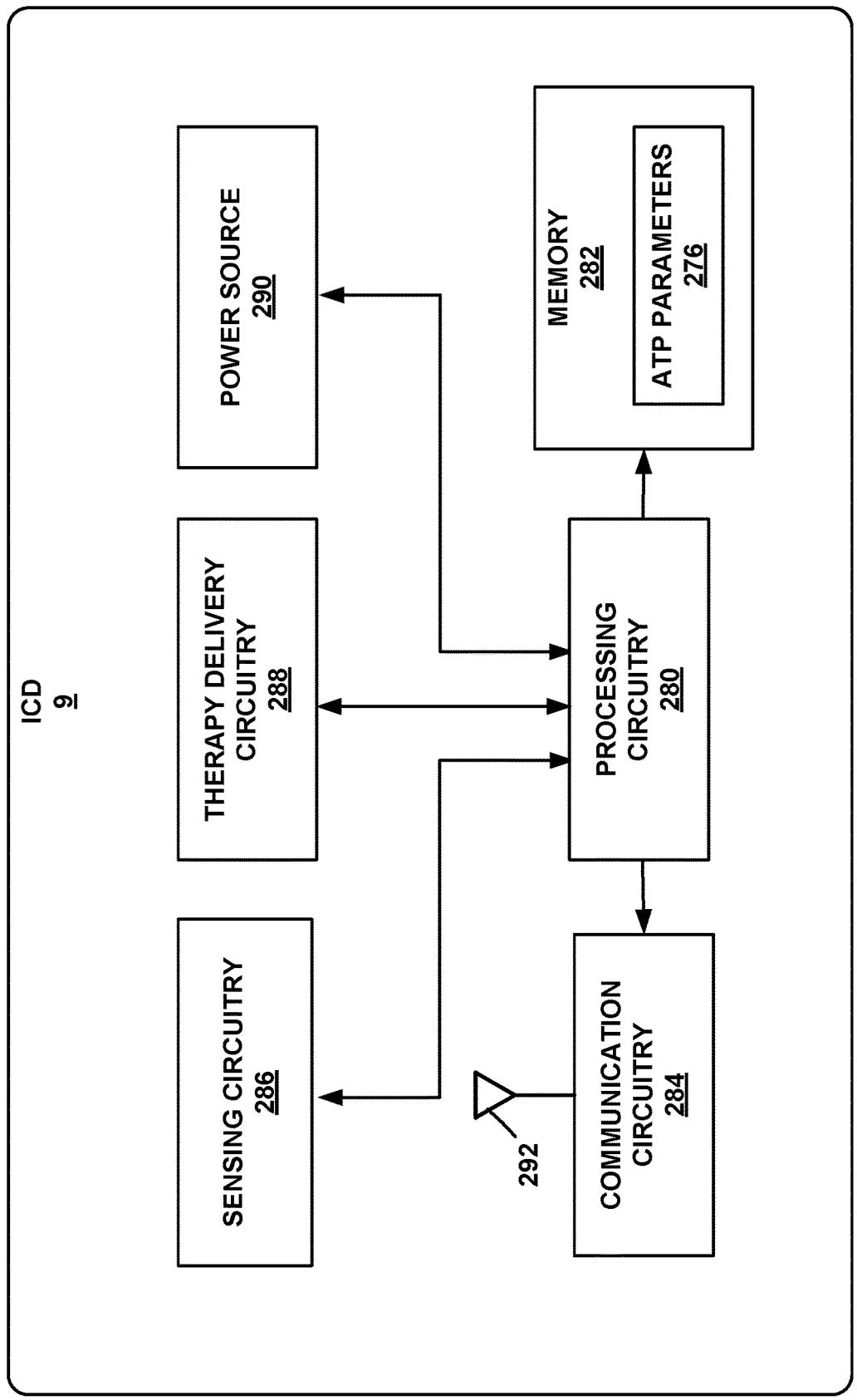
FIG. 6 is a functional block diagram illustrating an example configuration of the ICD of the implantable medical device system of FIGS. 1A-1C.

FIG. 6 is a functional block diagram illustrating an example configuration of ICD 9 of the implantable medical device system of FIGS. 1A-1C. In the illustrated example, ICD 9 includes processing circuitry 280, sensing circuitry 286, therapy delivery circuitry 288, communication circuitry 284, and memory 282. The electronic components may receive power from a power source 290, which may be a rechargeable or non-rechargeable battery. In other examples, ICD 9 may include more or fewer electronic components. The described circuitry may be implemented together on a common hardware component or separately as discrete but interoperable hardware or software components. Depiction of different features as circuitry is intended to highlight different functional aspects and does not necessarily imply that such circuitry must be realized by separate hardware or software components. Rather, functionality associated with one or more circuitry may be performed by separate hardware or software components, or integrated within common or separate hardware or software components. FIG. 6 will be described in the context of ICD 9 being coupled to lead 10 for exemplary purposes only. However, ICD 9 may be coupled to other leads, and thus other electrodes.

Memory 282 includes computer-readable instructions that, when executed by processing circuitry 282, cause ICD 9 and processing circuitry 280 to perform various functions attributed to ICD 9 and processing circuitry 280 herein (e.g., delivering anti-tachycardia pacing, sensing an evoked response, and/or modifying the ATP therapy). Memory 282 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Sensing circuitry 286 is electrically coupled to some or all of electrode 28 (or separately to segments 28a and/or 28b) and 32a and 32b via the conductors of lead 10 (shown in FIGS. 1A-1C) and one or more electrical feedthroughs, or to the housing electrode via conductors internal to the housing of ICD 9. Sensing circuitry 286 is configured to obtain signals sensed via one or more combinations of electrode 28 (or separately to segments 28a and/or 28b), 32a, 32b and the housing electrode of ICD 9 and process the obtained signals.

The components of sensing circuitry 286 may be analog components, digital components or a combination thereof. Sensing circuitry 286 may, for example, include one or more sense amplifiers, filters, rectifiers, threshold detectors, analog-to-digital converters (ADCs) or the like. Sensing circuitry 286 may convert the sensed signals to digital form and provide the digital signals to processing circuitry 280 for processing or analysis. For example, sensing circuitry 286 may amplify signals from the sensing electrodes and convert the amplified signals to multi-bit digital signals by an ADC. Sensing circuitry 286 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to processing circuitry 280.

Processing circuitry 280 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 280 may include multiple components, such as any combination of one or more microprocessors, one or more controllers, one or more DSPs, one or more ASICs, or one or more FPGAs, as well as other discrete or integrated logic circuitry. The functions attributed to processing circuitry 280 herein may be embodied as software, firmware, hardware or any combination thereof.

Processing circuitry 280 may process the signals from sensing circuitry 286 to monitor electrical activity of the heart of the patient. Processing circuitry 280 may store signals obtained by sensing circuitry 286 as well as any generated EGM waveforms, marker channel data or other data derived based on the sensed signals in memory 282. Processing circuitry 280 may analyze the EGM waveforms and/or marker channel data to detect cardiac events (e.g., tachycardia). In response to detecting the cardiac event, processing circuitry 280 may control therapy delivery circuitry 280 to deliver the desired therapy to treat the cardiac event, e.g., ATP therapy.

Therapy delivery circuitry 288 is configured to generate and deliver electrical stimulation therapy to the heart. Therapy delivery circuitry 288 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy delivery circuitry 288 may include a first set of components configured to provide pacing therapy and a second set of components configured to provide defibrillation therapy. In other instances, therapy delivery circuitry 288 may utilize the same set of components to provide both pacing and defibrillation therapy. In still other instances, therapy delivery circuitry 288 may share some of the defibrillation and pacing therapy components while using other components solely for defibrillation or pacing. In some examples, therapy delivery circuitry 288 may deliver pacing stimulation, e.g., ATP therapy, in the form of voltage or current electrical pulses. In other examples, therapy delivery circuitry 288 may deliver stimulation in the form of other signals, such as sine waves, square waves, or other substantially continuous time signals.

Processing circuitry 280 may control therapy delivery circuitry 288 to deliver the generated therapy to the heart via one or more combinations of electrode 28 (or separately to segments 28a and/or 28b), 32a, and 32b of lead 10 and the housing electrode of ICD 9 according to one or more therapy programs, which may be stored in memory 282. In instances in which processing circuitry 280 is coupled to a different lead, other electrodes may be utilized. Processing circuitry 280 controls therapy delivery circuitry 288 to generate electrical stimulation therapy with the amplitudes, pulse widths, timing, frequencies, electrode combinations or electrode configurations specified by stored therapy programs.

Processing circuitry 264 controls therapy delivery circuitry 288 to deliver cardiac pacing therapy to heart 26 according to parameters, which may be stored in memory 282. For example, processing circuitry 280 may control therapy delivery circuitry 288 to deliver pacing pulses with the amplitudes, pulse widths, frequency, or electrode polarities specified by the therapy parameters, including intervals that define under what conditions and when pacing pulses should be delivered.

Processing circuitry 280 may control therapy delivery circuitry 288 to deliver ATP therapy based on ATP parameters 276 stored in memory 282 and may modify the ATP therapy by modifying ATP parameters 276 in memory 282. ATP therapy parameters 276 may include pulse intervals, pulse width, current and/or voltage amplitudes, and durations for each pacing mode. For example, the pulse interval may be based on a fraction of the detected ventricular tachycardia (VT) cycle length and be between approximately 150 milliseconds and 500 milliseconds (e.g., between approximately 2.0 hertz and 7.0 hertz), and the pulse width may be between approximately 0.5 milliseconds and 2.0 milliseconds. The amplitude of each pacing pulse may be between approximately 2.0 volts and 10.0 volts. In some examples, the pulse amplitude may be approximately 6.0 V and the pulse width may be approximately 1.5 milliseconds; another example may include pulse amplitudes of approximately 5.0 V and pulse widths of approximately 1.0 milliseconds. Each train of pulses during ATP may last for a duration of between approximately 0.5 seconds to approximately 15 seconds or be defined as a specific number of pulses. Each pulse, or burst of pulses, may include a ramp up in amplitude or in pulse rate. In addition, trains of pulses in successive ATP periods may be delivered at increasing pulse rate in an attempt to capture the heart and terminate the tachycardia.

Therapy delivery circuitry 288 may include switch circuitry to select which of the available electrodes are used to deliver the therapy. The switch circuitry may include a switch array, switch matrix, multiplexer, or any other type of switching device suitable to selectively couple electrodes to therapy delivery circuitry 288. Processing circuitry 280 may select the electrodes to function as signal electrodes, or the signal vector, via the switch circuitry within therapy delivery circuitry 28. In instances in which defibrillation segments 28a and 28b are each coupled to separate conductors, processing circuitry 280 may be configured to selectively couples therapy delivery circuitry 288 to either one of segments 28a and 28b individually or couple to both of the segments 28a and 28b concurrently. In some instances, the same switch circuitry may be used by both therapy delivery circuitry 288 and sensing circuitry 286. In other instances, each of sensing circuitry 286 and therapy delivery circuitry 288 may have separate switch circuitry.

In one example, therapy delivery circuitry 288 may deliver pacing via an electrode vector that includes one or both defibrillation electrode segments 28a and 28b. The electrode vector used for pacing may be segment 28a as an anode (or cathode) and one of electrodes 28b, 32a, 32b, or the housing of ICD 9 as the cathode (or anode) or segment 28b as an anode (or cathode) and one of electrodes 28b, 32a, 32b, or the housing of ICD 9 as the cathode (or anode). In some examples, electrode 52 and/or electrode 60 of IPD 16 may be used as an anode or cathode and ICD 9 may communicate with 16 via communication circuitry 284 and/or external device may communicate with ICD 9 and IPD 16 to coordinate the use of electrodes of both ICD 9 and IPD 16.

Processing circuitry 280 controls therapy delivery circuitry 288 to generate and deliver pacing pulses with any of a number of shapes, amplitudes, pulse widths, or other characteristic to capture the heart. For example, the pacing pulses may be monophasic, biphasic, or multi-phasic (e.g., more than two phases). The pacing thresholds of the heart when delivering pacing pulses from the substernal space, e.g., from electrodes 32*a*, 32*b* and/or electrode segments 28*a* and/or 28*b* substantially within anterior mediastinum 36, may depend upon a number of factors, including location, type, size, orientation, and/or spacing of electrodes 32*a* and 32*b* and/or electrode segments 28*a* and 28*b*, location of ICD 9 relative to electrodes 32*a* and 32*b* and/or electrode segments 28*a* and 28*b*, physical abnormalities of the heart (e.g., pericardial adhesions or myocardial infarctions), or other factor(s).

Processing circuitry 280 may include a timing and control circuitry, which may be embodied as hardware, firmware, software, or any combination thereof. The timing and control circuitry may comprise a dedicated hardware circuit, such as an ASIC, separate from other processing circuitry 280 components, such as a microprocessor, or a software module executed by a component of processing circuitry 280, which may be a microprocessor or ASIC. The timing and control circuitry may implement programmable counters. If ICD 9 is configured to generate and deliver pacing pulses to heart 26, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control circuitry within processing circuitry 280 may include atrial and ventricular pacing escape intervals, refractory periods during which sensed P-waves and R-waves are ineffective to restart timing of the escape intervals, and the pulse widths of the pacing pulses. As another example, the timing and control circuitry may withhold sensing from one or more channels of sensing circuitry 286 for a time interval during and after delivery of electrical stimulation to heart 26. The durations of these intervals may be determined by processing circuitry 264 in response to stored data in memory 282. The timing and control circuitry of processing circuitry 264 may also determine the amplitude of the cardiac pacing pulses.

Interval counters implemented by the timing and control circuitry of processing circuitry 280 may be reset upon sensing of R-waves and P-waves with detection channels of sensing circuitry 286. In examples in which ICD 9 provides pacing, therapy delivery circuitry 288 may include pacer output circuits that are coupled to electrodes, for example, appropriate for delivery of a bipolar or unipolar pacing pulse to one of the chambers of heart 26. In such examples, processing circuitry 280 may reset the interval counters upon the generation of pacing pulses by therapy delivery circuitry 288, and thereby control the basic timing of cardiac pacing functions, including ATP or post-shock pacing.

The value of the count present in the interval counters when reset by sensed R-waves and P-waves may be used by processing circuitry 280 to measure the durations of R-R intervals, P-P intervals, P-R intervals and R-P intervals, which are measurements that may be stored in memory 282. Processing circuitry 280 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 282 may be configured as a plurality of recirculating buffers, capable of holding series of measured intervals, which may be analyzed by processing circuitry 280 in response to the occurrence of a pace or sense interrupt to determine whether the patient's heart 26 is presently exhibiting atrial or ventricular tachyarrhythmia.

In some examples, an arrhythmia detection method may include any suitable tachyarrhythmia detection algorithms. In some examples, processing circuitry 280 may determine that tachyarrhythmia has occurred by identification of shortened R-R (or P-P) interval lengths. Generally, processing circuitry 280 detects tachycardia when the interval length falls below 220 milliseconds and fibrillation when the interval length falls below 180 milliseconds. In other examples, processing circuitry 280 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 282. This interval length may need to be detected for a certain number of consecutive cycles, for a certain percentage of cycles within a running window, or a running average for a certain number of cardiac cycles, as examples. In other examples, additional physiological parameters may be used to detect an arrhythmia. For example, processing circuitry 280 may analyze one or more morphology measurements, impedances, or any other physiological measurements to determine that patient 14 is experiencing a tachyarrhythmia.

In the event that an ATP regimen is desired, timing intervals for controlling the generation of ATP therapies by therapy deliver circuitry 288 may be loaded by processing circuitry 280 into the timing and control circuitry based on ATP parameters 276 to control the operation of the escape interval counters therein and to define refractory periods during which detection of R-waves and P-waves is ineffective to restart the escape interval counters for the ATP. An ATP regimen may be desired if processing circuitry 280 detects an atrial or ventricular tachyarrhythmia based on signals from sensing circuitry 286, and/or receives a command from another device or system, such as IPD 16, as examples.

Memory 282 may be configured to store a variety of operational parameters, therapy parameters, including ATP therapy parameters 276, sensed and detected data, and any other information related to the therapy and treatment of patient 14. In the example of FIG. 6, memory 282 may store sensed ECGs, detected arrhythmias, communications from IPD 16, and therapy parameters that define ATP therapy (ATP therapy parameters 276). In other examples, memory 282 may act as a temporary buffer for storing data until it can be uploaded to IPD 16, another implanted device, or external device 21.

Communication circuitry 284 includes any suitable hardware, firmware, software or any combination thereof for communicating with another device, such as external device 21 (FIGS. 1A-1C and 7), IPD 16 (FIGS. 1A-1C and FIG. 2), a clinician programmer, a patient monitoring device, or the like. For example, communication circuitry 284 may include appropriate modulation, demodulation, frequency conversion, filtering, and amplifier components for transmission and reception of data with the aid of antenna 292. Antenna 292 may be located within connector block of ICD 9 or within the housing of ICD 9. Under the control of processing circuitry 280, communication circuitry 284 may receive downlink telemetry from and send uplink telemetry to external device 21 with the aid of antenna 292, which may be internal and/or external. Processing circuitry 280 may provide the data to be uplinked to external device 21 and the control signals for the telemetry circuit within communication circuitry 284, e.g., via an address/data bus. In some examples, communication circuitry 284 may provide received data to processing circuitry 280 via a multiplexer.

In some examples, ICD 9 may signal external device 21 to further communicate with and pass the alert through a network such as the Medtronic CareLink® Network developed by Medtronic, Inc., of Minneapolis, Minn., or some other network linking patient 14 to a clinician. ICD 9 may spontaneously transmit information to the network or in response to an interrogation request from a user.

Power source 290 may be any type of device that is configured to hold a charge to operate the circuitry of ICD 9. Power source 290 may be provided as a rechargeable or non-rechargeable battery. In other example, power source 290 may incorporate an energy scavenging system that stores electrical energy from movement of ICD 9 within patient 14.

The various circuitry of ICD 9 may include any one or more processors, controllers, digital signal processors (DSPs), application specific integrated circuits (ASICs), field programmable gate arrays (FPGAs), or equivalent discrete or integrated circuitry, including analog circuitry, digital circuitry, or logic circuitry.

According to the techniques of this disclosure, ICD 9 may deliver ATP therapy via therapy delivery circuitry 288, sense evoked response(s) of the heart to the delivered ATP therapy via sensing circuitry 286, determine latency metric(s) of the evoked response(s) via processing circuitry 280, and modify the ATP therapy based on the latency metric(s) via processing circuitry 280. The evoked response(s) may be detected as described above with reference to FIG. 5. The modification may be to a current pulse train of the ATP therapy and/or a subsequent pulse train of the ATP therapy. Processing circuitry 280 may modify the ATP therapy by modifying ATP parameters 276 stored in memory 282. The latency metric(s) may be local (based on evoked response(s) sensed at or near a location where the ATP therapy has been delivered) and/or the latency metric(s) may be global (based on evoked response(s) sensed further away from the location where the ATP therapy has been delivered). ICD 9 may work in coordination with IPD 16. For example, ICD 9 may deliver ATP therapy and sense evoked response(s) at one or more locations and IPD 16 may deliver ATP therapy and sense evoked response(s) at one or more different locations. In some examples, ICD 9 may deliver ATP therapy and sense evoked response(s) at the same or similar location to determine local latency metric(s) and IPD 16 may sense evoked response(s) to the therapy delivered by ICD 9 to determine global latency metrics. Communication circuitry 284 may allow ICD 9 to communicate with IPD 16 to provide for such coordination. In some examples, IPD 16 may determine latency metric(s) and communicate them to ICD 9. In some examples, IPD 16 may communicate sensed evoked response(s) to ICD 9 and processing circuitry 228 of ICD 9 may determine latency metric(s) based on the evoked response(s) information received from IPD 16.

In some examples, ICD 9 may perform the methods described herein without coordination with IPD 16. For example, a system may include extracardiovascular ICD system 6 but not IPD 16 and ICD system 6 may perform the methods described herein alone. In some, examples, system 8 may include extracardiovascular ICD system 6 and IPD 16 and extracardiovascular ICD system 6 may, at some times, perform the methods described herein in coordination with IPD 16 and, at other times, perform the methods described herein without the use of IPD 16. In examples in which ICD 9 may perform the methods described herein without coordination with IPD 16, ICD 9 may deliver ATP therapy via therapy delivery circuitry 288, sense evoked response(s) of the heart to the delivered ATP therapy via sensing circuitry 286, determine latency metric(s) of the evoked response(s) via processing circuitry 280, and modify the ATP therapy based on the latency metric(s) via processing circuitry 280. In such examples, processing circuitry 280 may be configured to determine the at least one latency metric by at least determining at least one morphological metric of an evoked response. For examples, processing circuitry 280 may be configured to determine the at least one latency metric by determining the time from stimulation delivery to the end of the QRS portion of the evoked response.

Figure 7:
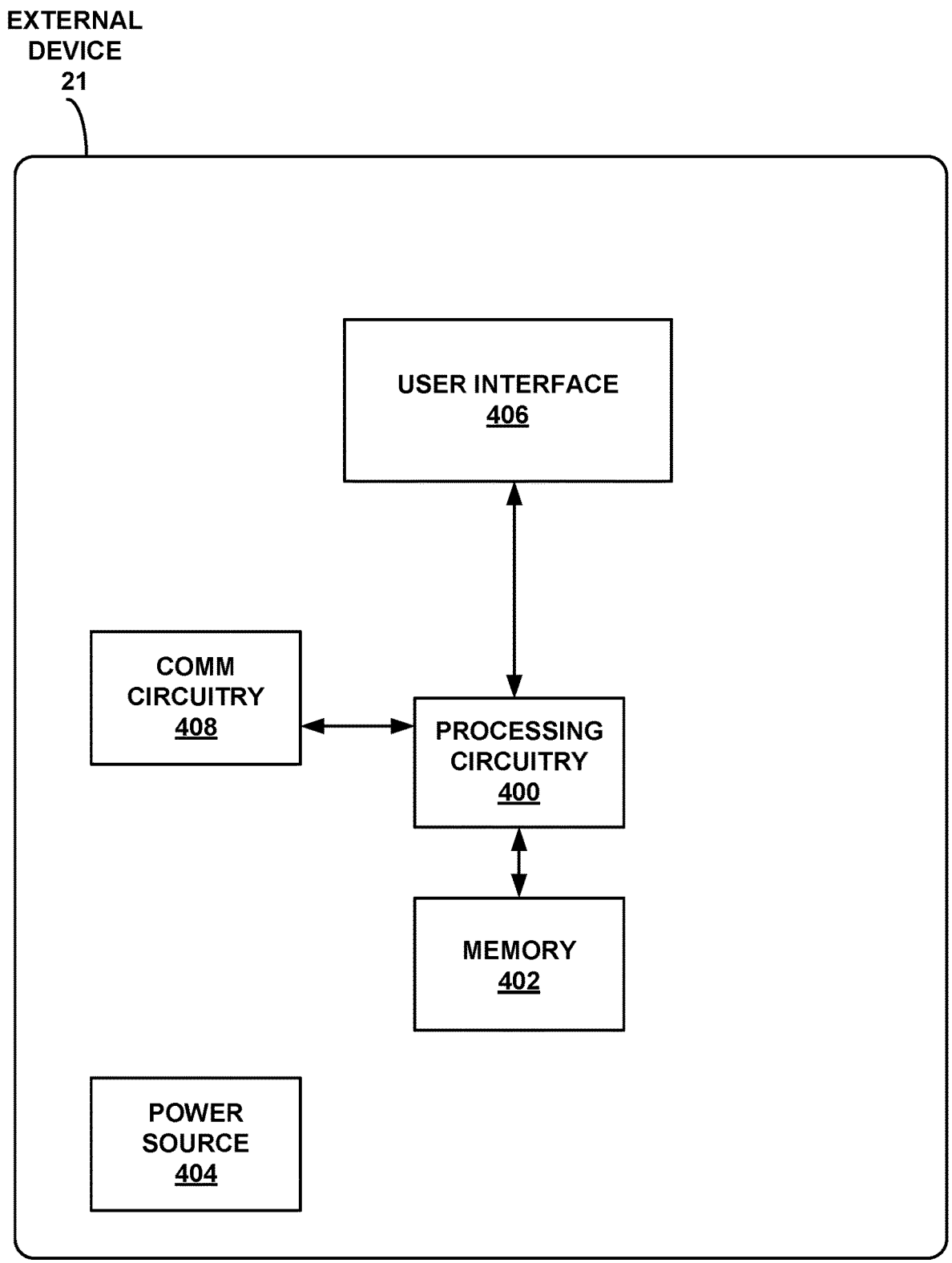
FIG. 7 is a functional block diagram illustrating an example configuration of the external device of FIGS. 1A-1C and FIG. 3.

FIG. 7 is a functional block diagram illustrating an example configuration of external device 21 of FIGS. 1A-1C and FIG. 3. External device 21 may include processing circuitry 400, memory 402, communication circuitry 408, user interface 406, and power source 404. Processing circuitry 400 controls user interface 406 and communication circuitry 408, and stores and retrieves information and instructions to and from memory 402. External device 21 may be configured for use as a clinician programmer or a patient programmer. Processing circuitry 400 may comprise any combination of one or more processors including one or more microprocessors, DSPs, ASICs, FPGAs, or other equivalent integrated or discrete logic circuitry. Accordingly, processing circuitry 400 may include any suitable structure, whether in hardware, software, firmware, or any combination thereof, to perform the functions ascribed herein to processing circuitry 400.

A user, such as a clinician or patient 14, may interact with external device 21 through user interface 406. User interface 406 may include a display, such as a LCD or LED display or other type of screen, to present information related the ATP therapy, including ATP therapy parameters 276 store in any of memory 266 and/or memory 282. In addition, user interface 406 may include an input mechanism to receive input from the user. The input mechanisms may include, for example, buttons, a keypad (e.g., an alphanumeric keypad), a peripheral pointing device or another input mechanism that allows the user to navigate though user interfaces presented by processing circuitry 400 of external device 21 and provide input.

If external device 21 includes buttons and a keypad, the buttons may be dedicated to performing a certain function, i.e., a power button, or the buttons and the keypad may be soft keys that change in function depending upon the section of the user interface currently viewed by the user. Alternatively, a screen of external device 21 may be a touch screen that allows the user to provide input directly to the user interface shown on the display. The user may use a stylus or a finger to provide input to the display. In other examples, user interface 406 also includes audio circuitry for providing audible instructions or sounds to patient 14 and/or receiving voice commands from patient 14, which may be useful if patient 14 has limited motor functions. Patient 14, a clinician or another user may also interact with external device 21 to manually select therapy programs, generate new therapy programs, modify therapy programs through individual or global adjustments, and transmit the new programs to PCD 110, IPD 16, and/or ICD 9.

In some examples, at least some of the control of therapy delivery by PCD 110, ICD 9, and/or IPD 16 may be implemented by processing circuitry 400 of external device 21. For example, in some examples, processing circuitry 400 may control delivery of ATP therapy by PCD 110, ICD 9, and/or IPD 16 by communicating with by PCD 110, ICD 9, and/or IPD 16 and may receive data regarding sensed signals and by communicating with by PCD 110, ICM 300, ICD 9, and/or IPD 16 to control therapy delivery circuitry of any of by PCD 110, ICD 9, and/or IPD 16. In some examples, memory 402 may store ATP therapy parameters 276, may use the parameters to control therapy delivery circuitry of by PCD 110, ICD 9, and/or IPD 16, and/or may modify ATP therapy parameters 276.

Memory 402 may include instructions for operating user interface 406 and communication circuitry 408, and for managing power source 404. Memory 402 may also store any therapy data retrieved from PCD 110 during the course of therapy. The clinician may use this therapy data to determine the progression of the patient condition in order to predict future treatment. Memory 402 may include any volatile or nonvolatile memory, such as RAM, ROM, EEPROM or flash memory. Memory 402 may also include a removable memory portion that may be used to provide memory updates or increases in memory capacities. A removable memory may also allow sensitive patient data to be removed before external device 21 is used by a different patient. In some examples, memory 402 may store ATP therapy parameters 276.

Wireless telemetry in external device 21 may be accomplished by RF communication or proximal inductive interaction of external device 21 with PCD 110, ICM 300, ICD 9, and/or IPD 16. This wireless communication is possible through the use of communication circuitry 408, which may communicate with a proprietary protocol or industry-standard protocol such as using the Bluetooth specification set. Accordingly, communication circuitry 408 may be similar to the communication circuitry contained within by PCD 110, ICD 9, and/or IPD 16. In alternative examples, external device 21 may be capable of infrared communication or direct communication through a wired connection. In this manner, other external devices may be capable of communicating with external device 21 without needing to establish a secure wireless connection.

Power source 404 may deliver operating power to the components of external device 21. Power source 404 may include a battery and a power generation circuit to produce the operating power. In some examples, the battery may be rechargeable to allow extended operation. Recharging may be accomplished by electrically coupling power source 308 to a cradle or plug that is connected to an alternating current (AC) outlet. In addition, recharging may be accomplished through proximal inductive interaction between an external charger and an inductive charging coil within external device 21. In other examples, traditional batteries (e.g., nickel cadmium or lithium ion batteries) may be used. In addition, external device 21 may be directly coupled to an alternating current outlet to operate. Power source 404 may include circuitry to monitor power remaining within a battery. In this manner, user interface 406 may provide a current battery level indicator or low battery level indicator when the battery needs to be replaced or recharged. In some cases, power source 404 may be capable of estimating the remaining time of operation using the current battery.

According to the techniques of this disclosure, external device 21 may be used to facilitate delivery and modification of ATP therapy with one or more of the devices described in this disclosure. For example, external device 21 may help to coordinate communication between devices and/or may be used to allow a user to observe and/or influence the ATP therapy delivery and modification.

Figure 8:
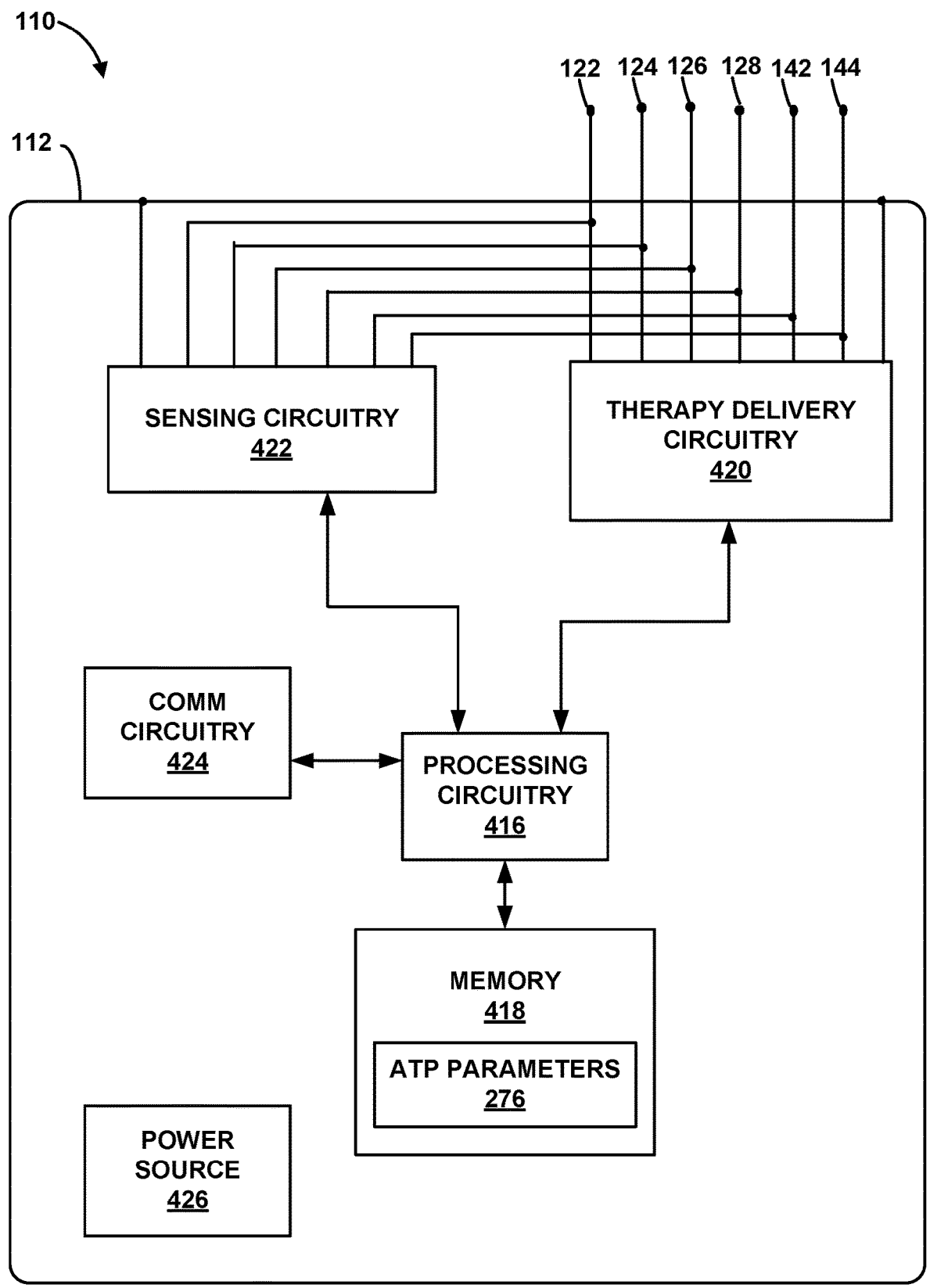
FIG. 8 is a functional block diagram illustrating an example configuration of the pacemaker/cardioverter/defibrillator (PCD) of the implantable medical device system of FIG. 3.

FIG. 8 is a functional block diagram illustrating an example configuration of pacemaker/cardioverter/defibrillator (PCD) 110 of the implantable medical device system of FIG. 3. As illustrated in FIG. 8, in one example, PCD 110 includes sensing circuitry 422, therapy delivery circuitry 420, processing circuitry 416 and associated memory 418, communication circuitry 424, and power source 426. The electronic components may receive power from power source 426, which may be a rechargeable or non-rechargeable battery. In other examples, PCD 110 may include more or fewer electronic components. The described circuitry may be implemented together on a common hardware component or separately as discrete but interoperable hardware or software components. Depiction of different features as circuitry is intended to highlight different functional aspects and does not necessarily imply that such circuitry must be realized by separate hardware or software components. Rather, functionality associated with one or more circuitry may be performed by separate hardware or software components, or integrated within common or separate hardware or software components.

Sensing circuitry 422 receives cardiac electrical signals from electrodes 112, 122, 124, 126, 128, 142 and 144 carried by the ventricular lead 120 and atrial lead 121, along with housing electrode 112 associated with the housing 112, for sensing cardiac events attendant to the depolarization of myocardial tissue, e.g. P-waves and R-waves. Sensing circuitry 422 may include a switch circuitry for selectively coupling electrodes 122, 124, 126, 128, 142, 144, and housing electrode 112 to sensing circuitry 422 in order to monitor electrical activity of heart 116. The switch circuitry may include a switch array, switch matrix, multiplexer, or any other type of switching device suitable to selectively couple one or more of the electrodes to sensing circuitry 422. In some examples, processing circuitry 416 selects the electrodes to function as sense electrodes, or the sensing vector, via the switch circuitry within sensing circuitry 422.

Sensing circuitry 422 may include multiple sensing channels, each of which may be selectively coupled to respective combinations of electrodes 122, 124, 126, 128, 142, 144 and housing 112 to detect electrical activity of a particular chamber of heart 116, e.g. an atrial sensing channel and a ventricular sensing channel. Each sensing channel may comprise a sense amplifier that outputs an indication to processing circuitry 416 in response to sensing of a cardiac depolarization, in the respective chamber of heart 116. In this manner, processing circuitry 416 may receive sense event signals corresponding to the occurrence of sensed R-waves and P-waves in the respective chambers of heart 116. Sensing circuitry 422 may further include digital signal processing circuitry for providing processing circuitry 416 with digitized EGM signals, which may be used for cardiac rhythm discrimination.

The components of sensing circuitry 422 may be analog components, digital components or a combination thereof. Sensing circuitry 422 may, for example, include one or more sense amplifiers, filters, rectifiers, threshold detectors, analog-to-digital converters (ADCs) or the like. Sensing circuitry 422 may convert the sensed signals to digital form and provide the digital signals to processing circuitry 416 for processing or analysis. For example, sensing circuitry 422 may amplify signals from the sensing electrodes and convert the amplified signals to multi-bit digital signals by an ADC. Sensing circuitry 422 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to processing circuitry 416.

Sensing circuitry 422 and/or processing circuitry 416 may also include circuitry for measuring the capture threshold for the delivery of pacing pulses via electrodes 122, 124, 126, 128, 142, 144, and 112. The capture threshold may indicate the voltage and pulse width necessary to induce depolarization of the surrounding cardiac muscle. For example, processing circuitry 416 may periodically control therapy delivery circuitry 420 to modify the amplitude of pacing pulses delivered to a patient, and sensing circuitry 422 and/or processing circuitry 416 may detect whether the surrounding cardiac tissue depolarized in response to the pacing pulses, i.e., detected whether there was an evoked response to the pacing pulse. Processing circuitry 416 may determine the capture threshold based on the amplitude where loss of capture occurred. Processing circuitry 416 may also determine one or more latency metrics based on detecting the evoked response to ATP therapy pulses, as described in greater detail below. In addition to detecting and identifying specific types of cardiac rhythms, sensing circuitry 422 may also sample the detected intrinsic signals to generate an electrogram or other time-based indication of cardiac events.

Processing circuitry 416 may process the signals from sensing circuitry 422 to monitor electrical activity of the heart of the patient. Processing circuitry 416 may store signals obtained by sensing circuitry 422 as well as any generated EGM waveforms, marker channel data or other data derived based on the sensed signals in memory 418. Processing circuitry 416 may analyze the EGM waveforms and/or marker channel data to detect cardiac events (e.g., tachycardia). In response to detecting the cardiac event, processing circuitry 416 may control therapy delivery circuitry 420 to deliver the desired therapy to treat the cardiac event, e.g., ATP therapy.

In examples in which PCD 110 includes more than two electrodes, therapy delivery circuitry 420 may include a switch and processing circuitry 416 may use the switch to select, e.g., via a data/address bus, which of the available electrodes are used to deliver pacing pulses. The switch may include a switch array, switch matrix, multiplexer, or any other type of switching device suitable to selectively couple stimulation energy to selected electrodes. Processing circuitry 416 may select the electrodes to function as signal electrodes, or the signal vector, via the switch circuitry within therapy delivery circuitry 420. In some instances, the same switch circuitry may be used by both therapy delivery circuitry 420 and sensing circuitry 422. In other instances, each of sensing circuitry 422 and therapy delivery circuitry 420 may have separate switch circuitry.

Memory 418 may include computer-readable instructions that, when executed by processing circuitry 416, cause PCD 110 to perform various functions attributed throughout this disclosure to PCD 110 and processing circuitry 416. The computer-readable instructions may be encoded within memory 418. Memory 418 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 416 may include any one or more of a microprocessor, a controller, a digital signal processor (DSP), an application specific integrated circuit (ASIC), a field-programmable gate array (FPGA), or equivalent discrete or integrated logic circuitry or state machine. In some examples, processing circuitry 416 may include multiple components, such as any combination of one or more microprocessors, one or more controllers, one or more DSPs, one or more ASICs, or one or more FPGAs, as well as other discrete or integrated logic circuitry or state machines. The functions attributed to processing circuitry 416 herein may be embodied as software, firmware, hardware or any combination thereof.

Therapy delivery circuitry 420 is electrically coupled to electrodes 122, 124, 126, 128, 142, 144, and 112. In the illustrated example, therapy delivery circuitry 420 is configured to generate and deliver electrical stimulation therapy to a heart of a patient. For example, therapy delivery circuitry 420 may deliver the electrical stimulation therapy to a portion of cardiac muscle within the heart via any combination of electrodes 122, 124, 126, 128, 142, 144, and 112. In some examples, therapy delivery circuitry 420 may deliver pacing stimulation, e.g., ATP therapy, in the form of voltage or current electrical pulses. In other examples, therapy delivery circuitry 420 may deliver stimulation in the form of other signals, such as sine waves, square waves, or other substantially continuous time signals.

Although PCD 110 is generally described as delivering pacing pulses, PCD 110 may deliver cardioversion or defibrillation pulses in other examples. Therapy delivery circuitry 420 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy delivery circuitry 420 may include a first set of components configured to provide pacing therapy and a second set of components configured to provide defibrillation therapy. In other instances, therapy delivery circuitry 420 may utilize the same set of components to provide both pacing and defibrillation therapy. In still other instances, therapy delivery circuitry 420 may share some of the defibrillation and pacing therapy components while using other components solely for defibrillation or pacing.

Processing circuitry 416 may control therapy delivery circuitry 420 to deliver electrical stimulation therapy, e.g., anti-tachyarrhythmia therapy, post-shock pacing, etc., to heart 116 according to therapy parameters, which may be stored in memory 418. Therapy delivery circuitry 420 is electrically coupled to electrodes 122, 124, 126, 128, 142, 144 and housing electrode 112 (all of which are shown in FIGS. 3 and 8). Therapy delivery circuitry 420 is configured to generate and deliver electrical stimulation therapy to heart 116 via selected combinations of electrodes 122, 124, 126, 128, 142, 144, and housing electrode 112.

Processing circuitry 416 may control therapy delivery circuitry 420 to deliver pacing pulses for ATP therapy according to ATP parameters 276 stored in memory 418. ATP therapy parameters 276 may include pulse intervals, pulse width, current and/or voltage amplitudes, and durations for each pacing mode. For example, the pulse interval may be based on a fraction of the detected ventricular tachycardia (VT) cycle length and be between approximately 150 milliseconds and 500 milliseconds (e.g., between approximately 2.0 hertz and 7.0 hertz), and the pulse width may be between approximately 0.5 milliseconds and 2.0 milliseconds. The amplitude of each pacing pulse may be between approximately 2.0 volts and 10.0 volts. In some examples, the pulse amplitude may be approximately 6.0 V and the pulse width may be approximately 1.5 milliseconds; another example may include pulse amplitudes of approximately 5.0 V and pulse widths of approximately 1.0 milliseconds. Each train of pulses during ATP may last for a duration of between approximately 0.5 seconds to approximately 15 seconds or be defined as a specific number of pulses. Each pulse, or burst of pulses, may include a ramp up in amplitude or in pulse rate. In addition, trains of pulses in successive ATP periods may be delivered at increasing pulse rate in an attempt to capture the heart and terminate the tachycardia.

Processing circuitry 416 controls therapy delivery circuitry 420 to generate and deliver pacing pulses with any of a number of shapes, amplitudes, pulse widths, or other characteristic to capture the heart. For example, the pacing pulses may be monophasic, biphasic, or multi-phasic (e.g., more than two phases). The pacing thresholds of the heart when delivering pacing pulses may depend upon a number of factors, including location, type, size, orientation, and/or spacing of PCD 110 and/or electrodes 122, 124, 126, 128, 142, 144, and 122, physical abnormalities of the heart (e.g., pericardial adhesions or myocardial infarctions), or other factor(s).

In examples in which PCD 110 includes more than two electrodes, therapy delivery circuitry 420 may include a switch and processing circuitry 416 may use the switch to select, e.g., via a data/address bus, which of the available electrodes are used to deliver pacing pulses. The switch may include a switch array, switch matrix, multiplexer, or any other type of switching device suitable to selectively couple stimulation energy to selected electrodes.

Memory 418 stores ATP therapy parameters 276, including intervals, counters, or other data used by processing circuitry 416 to control the delivery of pacing pulses by therapy delivery circuitry 420. Such data may include intervals and counters used by processing circuitry 416 to control the delivery of pacing pulses to heart 116. The intervals and/or counters are, in some examples, used by processing circuitry 416 to control the timing of delivery of pacing pulses relative to an intrinsic or paced event in another chamber. ATP therapy parameters 276 may also include intervals for controlling cardiac sensing functions such as blanking intervals and refractory sensing intervals and counters for counting sensed events for detecting cardiac rhythm episodes. Events sensed by sense amplifiers included in sensing circuitry 422 are identified in part based on their occurrence outside a blanking interval and inside or outside of a refractory sensing interval. Events that occur within predetermined interval ranges are counted for detecting cardiac rhythms. According to examples described herein, sensing circuitry 422, memory 418, and processing circuitry 416 are configured to use timers and counters for measuring sensed event intervals and determining event patterns for use in detecting possible ventricular lead dislodgement.

Memory 418 may be further configured to store sensed and detected data, and any other information related to the therapy and treatment of a patient. In the example of FIG. 8, memory 418 may store sensed ECGs, detected arrhythmias, communications from PCD 100. In other examples, memory 418 may act as a temporary buffer for storing data until it can be uploaded to another implanted device, or external device 21.

Communication circuitry 424 is used to communicate with external device 21 and/or ICM 300 for transmitting data accumulated by PCD 110 and for receiving interrogation and programming commands to and/or from external device 21 and/or ICM 300. Communication circuitry 268 includes any suitable hardware, firmware, software or any combination thereof for communicating with another device, such as external device 21 (FIGS. 1A-1C and 7), ICM 300 (FIGS. 3 and 9), a clinician programmer, a patient monitoring device, or the like. For example, communication circuitry 424 may include appropriate modulation, demodulation, frequency conversion, filtering, and amplifier components for transmission and reception of data. Under the control of processing circuitry 416, communication circuitry 424 may receive downlink telemetry from and send uplink telemetry to external device 21 with the aid of an antenna, which may be internal and/or external. Processing circuitry 416 may provide the data to be uplinked to external device 21 and the control signals for the telemetry circuit within communication circuitry 424, e.g., via an address/data bus. In some examples, communication circuitry 424 may provide received data to processing circuitry 416 via a multiplexer.

In some examples, PCD 110 may signal external device 21 to further communicate with and pass the alert through a network such as the Medtronic CareLink® Network developed by Medtronic, Inc., of Minneapolis, Minn., or some other network linking a patient to a clinician. PCD 110 may spontaneously transmit information to the network or in response to an interrogation request from a user.

Power source 426 may be any type of device that is configured to hold a charge to operate the circuitry of PCD 110. Power source 426 may be provided as a rechargeable or non-rechargeable battery. In other example, power source 426 may incorporate an energy scavenging system that stores electrical energy from movement of PCD 110 within patient 114.

The various circuitry of PCD 110 may include any one or more processors, controllers, digital signal processors (DSPs), application specific integrated circuits (ASICs), field programmable gate arrays (FPGAs), or equivalent discrete or integrated circuitry, including analog circuitry, digital circuitry, or logic circuitry.

According to the techniques of this disclosure, PCD 100 may deliver ATP therapy via therapy delivery circuitry 420, sense evoked response(s) of the heart to the delivered ATP therapy via sensing circuitry 422, determine latency metric(s) of the evoked response(s) via processing circuitry 416, and modify the ATP therapy based on the latency metric(s) via processing circuitry 416. The evoked response(s) may be detected as described above with reference to FIG. 5. The modification may be to a current pulse train of the ATP therapy and/or a subsequent pulse train of the ATP therapy. Processing circuitry 416 may modify the ATP therapy by modifying ATP parameters 276 stored in memory 418. The latency metric(s) may be local (based on evoked response(s) sensed at or near a location where the ATP therapy has been delivered) and/or the latency metric(s) may be global (based on evoked response(s) sensed further away from the location where the ATP therapy has been delivered). PCD 110 may work in coordination with ICM 300. For example, PCD 110 may deliver ATP therapy and sense evoked response(s) at one or more locations and ICM 300 may sense evoked response(s) at one or more different locations. In some examples, PCD 110 may deliver ATP therapy and sense evoked response(s) at the same or similar location to determine local latency metric(s) and ICM 300 may sense evoked response(s) to the therapy delivered by PCD 110 to determine global latency metrics. Communication circuitry 424 may allow PCD 110 to communicate with ICM 300 to provide for such coordination. In some examples, ICM 300 may determine latency metric(s) and communicate them to PCD 110. In some examples, ICM 300 may communicate sensed evoked response(s) to PCD 100 and processing circuitry 416 of PCD 110 may determine latency metric(s) based on the evoked response(s) information received from ICM 300.

Figure 9:
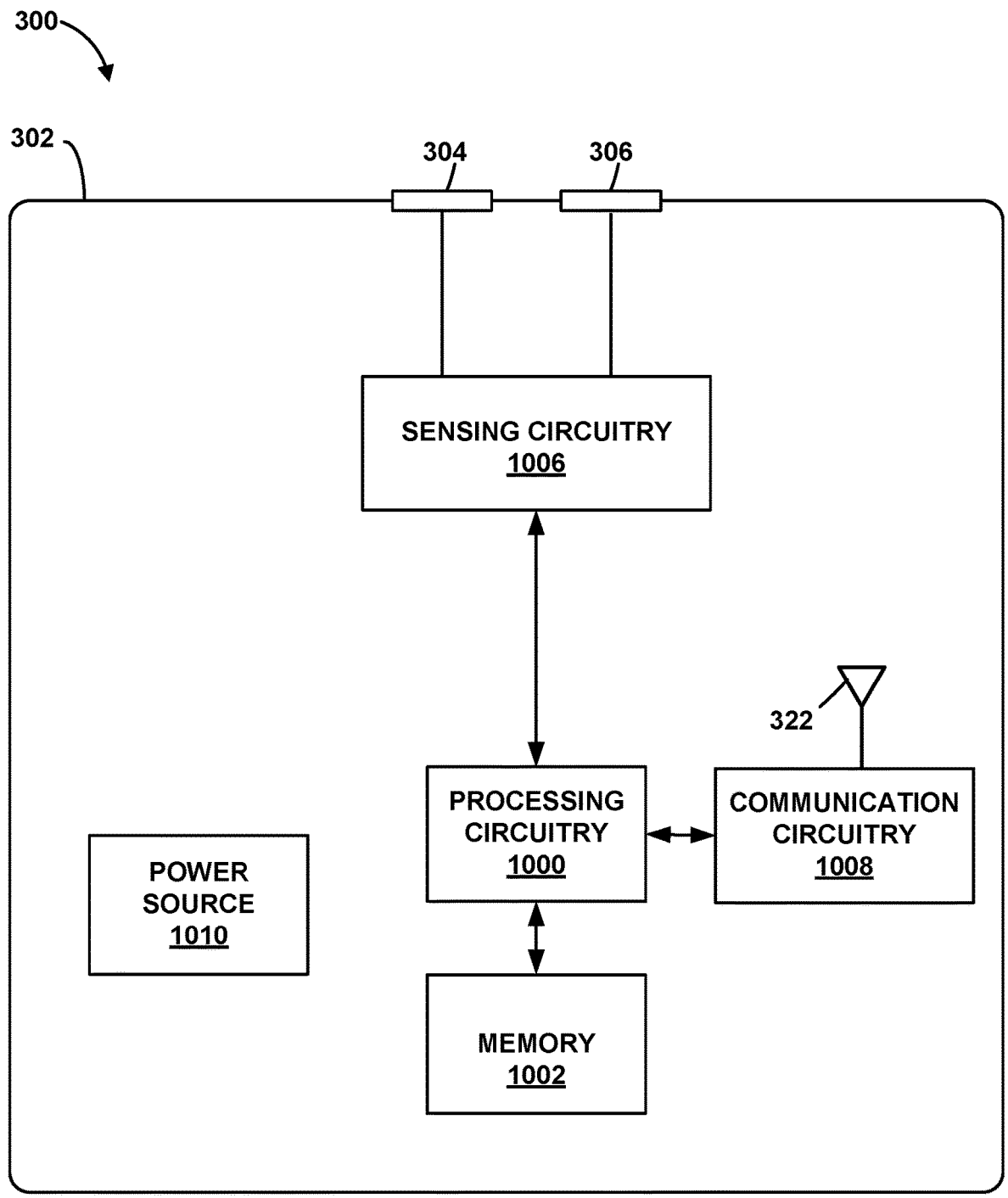
FIG. 9 is a functional block diagram illustrating an example configuration of the ICM of FIGS. 1A-1C and FIG. 4.

FIG. 9 is a functional block diagram illustrating an example configuration of ICM 300 of FIGS. 1A-1C and FIG. 4. In the illustrated example, ICM 300 includes processing circuitry 1000, memory 1002, sensing circuitry 1006, communication circuitry 1008 connected to antenna 322, and power source 1010. The electronic components may receive power from a power source 1010, which may be a rechargeable or non-rechargeable battery. In other examples, ICM 300 may include more or fewer electronic components. The described circuitry may be implemented together on a common hardware component or separately as discrete but interoperable hardware or software components. Depiction of different features as circuitry is intended to highlight different functional aspects and does not necessarily imply that such circuitry must be realized by separate hardware or software components. Rather, functionality associated with one or more circuitry may be performed by separate hardware or software components, or integrated within common or separate hardware or software components.

Memory 1002 includes computer-readable instructions that, when executed by processing circuitry 1000, cause ICM 300 and processing circuitry 1000 to perform various functions attributed to ICM 300 and processing circuitry 1000 herein (e.g., sensing an evoked response and/o determining a latency metric based on the evoked response). Memory 1002 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 1002 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 100 may include multiple components, such as any combination of one or more microprocessors, one or more controllers, one or more DSPs, one or more ASICs, or one or more FPGAs, as well as other discrete or integrated logic circuitry. The functions attributed to processing circuitry 1000 herein may be embodied as software, firmware, hardware or any combination thereof.

Processing circuitry 1000 controls sensing circuitry 1006 to sense evoked responses of the heart via electrodes 304 and 306. Although ICM 300 may only include two electrodes, e.g., electrodes 304 and 306, ICM 300 may utilize three or more electrodes in other examples. ICM 300 may use any combination of electrodes to detect electrical signals from patient 114. Sensing circuitry 1006 is electrically coupled to electrodes 304 and 306 carried on housing 302 of ICM 300. Processing circuitry 1000 may also determine one or more latency metrics based on detecting the evoked response to ATP therapy pulses, as described in greater detail below Sensing circuitry 1006 is electrically connected to and monitors signals from one or more of electrodes 304 and 306 in order to monitor electrical activity of a heart, impedance, or other electrical phenomenon. Sensing may be done to determine heart rates or heart rate variability, or to detect arrhythmias (e.g., tachyarrhythmias or bradycardia) or other electrical signals. Sensing circuitry 1004 may also include a switch to select which of the available electrodes (or electrode polarity) are used to sense the heart activity, depending upon which electrode combination, or electrode vector, is used in the current sensing configuration. In examples with several electrodes, processing circuitry 1000 may select the electrodes that function as sense electrodes, i.e., select the sensing configuration, via the switch circuitry within sensing circuitry 1004. Sensing circuitry 1004 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processing circuitry 1000, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processing circuitry 1000 may control the functionality of sensing circuitry 1006 by providing signals via a data/address bus.

The components of sensing circuitry 1006 may be analog components, digital components or a combination thereof. Sensing circuitry 1006 may, for example, include one or more sense amplifiers, filters, rectifiers, threshold detectors, analog-to-digital converters (ADCs) or the like. Sensing circuitry 1006 may convert the sensed signals to digital form and provide the digital signals to processing circuitry 1000 for processing or analysis. For example, sensing circuitry 1006 may amplify signals from the sensing electrodes and convert the amplified signals to multi-bit digital signals by an ADC. Sensing circuitry 1006 may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to processing circuitry 1000.

Processing circuitry 1000 may implement programmable counters and may withhold sensing from one or more channels of sensing circuitry 1006 for a time interval during and after delivery of electrical stimulation to heart 116. The durations of these intervals may be determined by processing circuitry 1000 in response to stored data in memory 1002.

Interval counters implemented by processing circuitry 1000 may be reset upon sensing of R-waves and P-waves with detection channels of sensing circuitry 1006. The value of the count present in the interval counters when reset by sensed R-waves and P-waves may be used by processing circuitry 1000 to measure the durations of R-R intervals, P-P intervals, P-R intervals and R-P intervals, which are measurements that may be stored in memory 1002. Processing circuitry 1000 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 1002 may be configured as a plurality of recirculating buffers, capable of holding series of measured intervals, which may be analyzed by processing circuitry 1000 in response to the occurrence of a sense interrupt to determine whether the patient's heart 116 is presently exhibiting atrial or ventricular tachyarrhythmia.

In some examples, an arrhythmia detection method may include any suitable tachyarrhythmia detection algorithms. In one example, processing circuitry 1000 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. are incorporated herein by reference in their entireties. However, other arrhythmia detection methodologies, such as those methodologies that utilize timing and morphology of the electrocardiogram, may also be employed by processing circuitry 1000 in other examples.

In some examples, processing circuitry 1000 may determine that tachyarrhythmia has occurred by identification of shortened R-R (or P-P) interval lengths. Generally, processing circuitry 1000 detects tachycardia when the interval length falls below 220 milliseconds and fibrillation when the interval length falls below 180 milliseconds. In other examples, processing circuitry 1000 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 1002. This interval length may need to be detected for a certain number of consecutive cycles, for a certain percentage of cycles within a running window, or a running average for a certain number of cardiac cycles, as examples. In other examples, additional physiological parameters may be used to detect an arrhythmia. For example, processing circuitry 1000 may analyze one or more morphology measurements, impedances, or any other physiological measurements to determine that patient 114 is experiencing a tachyarrhythmia.

In addition to detecting and identifying specific types of cardiac rhythms, sensing circuitry 1004 may also sample the detected intrinsic signals to generate an electrogram or other time-based indication of cardiac events. Processing circuitry 1000 may also be able to coordinate the delivery of pacing pulses from another device, such as PCD 110. For example, processing circuitry 1000 may identify delivered pulses from PCD 110 via sensing circuitry 1006 and update pulse timing to accomplish a selected pacing regimen. This detection may be on a pulse-to-pulse or beat-to-beat basis, or on a less frequent basis to make slight modifications to pulse rate over time. In other examples, IPDs may communicate with each other via communication circuitry 1008 and/or instructions over a carrier wave (such as a stimulation waveform). In this manner, ATP pacing may be coordinated by multiple devices.

Memory 1002 may be configured to store a variety of sensed and detected data and any other information related to the therapy and treatment of patient 114. In the example of FIG. 9, memory 1002 may store sensed ECGs and/or detected arrhythmias, communications from PCD 110. In other examples, memory 1002 may act as a temporary buffer for storing data until it can be uploaded to PCD 110, another implanted device, or external device 21.

Communication circuitry 1008 includes any suitable hardware, firmware, software or any combination thereof for communicating with another device, such as external device 21, PCD 110 (FIGS. 1A-1C).), a clinician programmer, a patient monitoring device, or the like. For example, communication circuitry 1008 may include appropriate modulation, demodulation, frequency conversion, filtering, and amplifier components for transmission and reception of data. Under the control of processing circuitry 1000, communication circuitry 1008 may receive downlink telemetry from and send uplink telemetry to external device 21 with the aid of antenna 322, which may be internal and/or external. Processing circuitry 100 may provide the data to be uplinked to external device 21 and the control signals for the telemetry circuit within communication circuitry 1008, e.g., via an address/data bus. In some examples, communication circuitry 1008 may provide received data to processing circuitry 1000 via a multiplexer.

In some examples, ICM 300 may signal external device 21 to further communicate with and pass the alert through a network such as the Medtronic CareLink® Network developed by Medtronic, Inc., of Minneapolis, Minn., or some other network linking patient 114 to a clinician. ICM 300 may spontaneously transmit information to the network or in response to an interrogation request from a user.

Power source 1010 may be any type of device that is configured to hold a charge to operate the circuitry of ICM 300. Power source 1010 may be provided as a rechargeable or non-rechargeable battery. In other example, power source 1010 may incorporate an energy scavenging system that stores electrical energy from movement of ICM 200 within patient 114.

The various circuitry of IPD 16 may include any one or more processors, controllers, digital signal processors (DSPs), application specific integrated circuits (ASICs), field programmable gate arrays (FPGAs), or equivalent discrete or integrated circuitry, including analog circuitry, digital circuitry, or logic circuitry.

According to the techniques of this disclosure, PCD 110 may deliver ATP therapy and sense evoked response(s) at one or more locations and ICM 300 may sense evoked response(s) at one or more different locations via sensing circuitry 1006. The evoked response(s) may be detected as described above with reference to FIG. 5. In some examples, PCD 110 may deliver ATP therapy and sense evoked response(s) at the same or similar location to determine local latency metric(s) and ICM 300 may sense evoked response(s) to the therapy delivered by PCD 110 to determine global latency metrics. Communication circuitry 1008 may allow ICM 300 to communicate with PCD 110 to provide for such coordination. In some examples, ICM 300 may determine latency metric(s) via processing circuitry 1000 and communicate them to PCD 110 via communication circuitry 1008. In some examples, ICM 300 may communicate sensed evoked response(s) to PCD 100 and processing circuitry 416 of PCD 110 may determine latency metric(s) based on the evoked response(s) information received from ICM 300.

Figure 10:
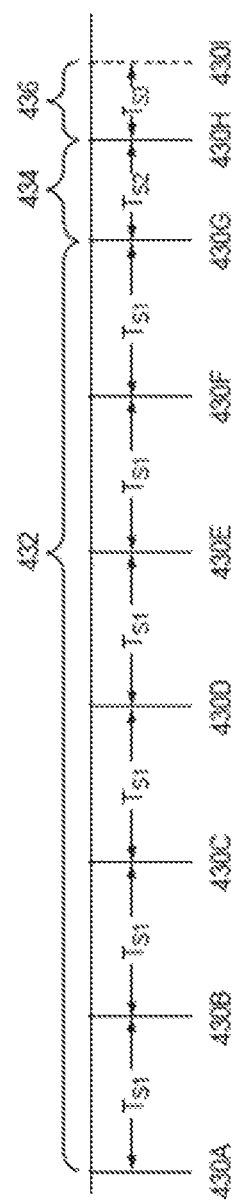
FIG. 10 is a timing diagram illustrating delivery of a plurality of pulses delivered as ATP therapy.

FIG. 10 is a timing diagram illustrating delivery of a plurality of pulses delivered as ATP therapy. Times 430A-430I may be times associated with delivery of pacing pulses at different portions of the ATP therapy. Time 430A may indicate a time at which the ATP therapy is initiated and a first pulse of a train of ATP pulses of the ATP therapy is delivered. Time 430B may indicate a time at which a second pulse of the ATP therapy is delivered. Any suitable time interval may separate time 430A and time 430B. In the illustrated example, the time separating time 430A and time 430B is noted as $T_{S1}$. A plurality of phases of the ATP therapy may involve delivery of one or more pulses. During phase 432, a plurality of pulses may be delivered at times 430A, 430B, 430C, 430D, 430F, and 430G. During phase 432, each subsequently delivered pulse may be separated by substantially the same time interval of $T_{S1}$. During phase 434, a single pulse may be delivered at time 430H, which may be separated from time 430G by the time interval of $T_{S2}$, which may be different than $T_{S1}$. For example, $T_{S2}$ may be less than $T_{S1}$. During phase 436, a single pulse may be delivered at time 430U, which may be separated from time 430H by the time interval of $T_{S3}$, which may be different than $T_{S1}$ and/or $T_{S2}$. For example, $T_{S3}$ may be less than $T_{S1}$ and $T_{S2}$. ATP therapy may be delivered in such a fashion, with decreasing time intervals between pulses, to advance the heart to refractory. However, decreasing the time interval between pulses can also lead to loss of capture and may result in delivery of wasteful pulses, as well as waste of time. The systems and methods described herein may be used to modify ATP therapy appropriately before loss of capture occurs to prevent loss of capture, prevent delivery of unnecessary pulses, and save time. ATP therapy pulses may be delivered by any device or combination of devices, such as the devices in the systems described above.

Figure 11A:
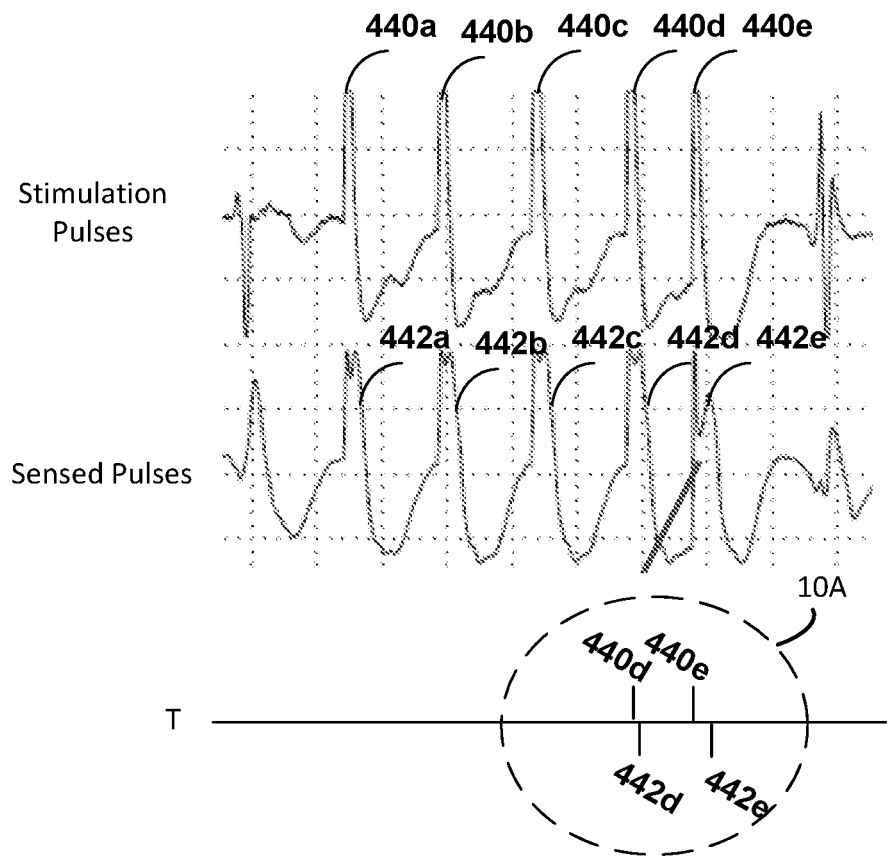
FIG. 11A illustrates left and right ventricular electrocardiograms and a corresponding timing diagram, which illustrate a plurality of delivered pacing pulses and a plurality of sensed evoked responses.
Figure 11B:
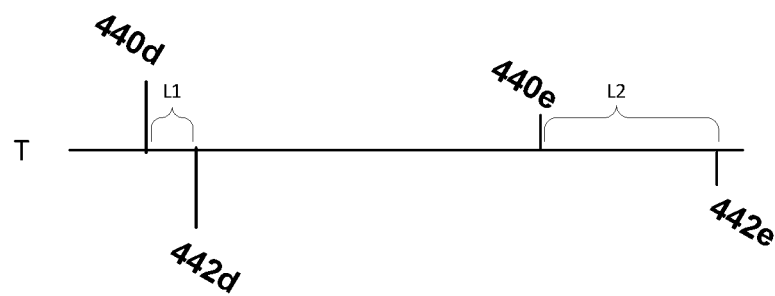
FIG. 11B is a timing diagram corresponding to a portion of the electrocardiogram of FIG. 11A.

FIG. 11A illustrates electrocardiograms of stimulation pulses and sensed pulses and a corresponding timing diagram, which illustrate a plurality of delivered pacing pulses and a plurality of sensed evoked responses. FIG. 11B is a timing diagram corresponding to a portion of the electrocardiogram of FIG. 11A. Pacing pulses 440a-440e may be stimulation pulses delivered to the heart by therapy delivery circuitry of any of the devices described herein as part of ATP therapy including one or more pulse trains each including a plurality of pacing pulses, such as pacing pulses 440a-440e. ATP parameters 276 may be used to define delivery of pacing pulses 440 and may be stored in a memory such as the memory of any of the devices described above. Evoked responses 422a-422e may represent depolarizations resulting from pacing pulses 440a, 440b, 440c, 440d, and 444e. Pacing pulses 440a-440e may be delivered using any electrodes and therapy delivery circuitry of any suitable device, including the devices described above. Evoked responses 422a, 422b, 442c, 442d, and 422e may be sensed using any electrodes and any sensing circuitry of any suitable device, including the devices described above. Pacing pulses 440 may be delivered with shorter and shorter intervals between pacing pulses 440 to lead to refractory of heart 26. However, this may result in loss of capture.

The techniques described herein may allow for modification of ATP therapy, e.g., by modification of ATP therapy parameters, 276 to prevent loss of capture, unnecessary pacing pulses, and/or longer time to tachyarrhythmia termination. For example, processing circuitry, such as the processing circuitry of any of the devices described above, may detect at least one evoked response to at least one of a plurality of pacing pulses, such as 440a, 440b, 440c, 440d, and 444e. The evoked response(s) may be detected as described above with reference to FIG. 5. The processing circuitry may determine at least one latency metric for at least one of the plurality of pacing pulses, such as pacing pulses 440a, 440b, 440c, 440d, and 444e, of at least one of the one or more pulse trains based on the evoked responses. The processing circuitry may modify the ATP therapy based on the at least one latency metric. For example, the processing circuitry may modify the ATP therapy based on the at least one latency metric to prevent loss of capture. This process may be performed by the various devices described above with reference to FIGS. 5-9.

For example, processing circuitry may determine the at least one latency metric by at least determining an interval between a pacing pulse 440 and an evoked response 442. For example, as shown in FIG. 11B, the processing circuitry may determine an interval L1 between pacing pulse 440d and evoked response 442d and may determine an interval L2 between pacing pulse 440e and evoked response 442e. In some examples, the processing circuitry may compare one or both of the intervals to a threshold and modify the ATP therapy if the interval exceeds the threshold. For example, the processing circuitry may compare the interval L2 to a threshold such as L1, or to a threshold such as L1+an additional amount, and may modify the ATP therapy is the interval exceeds the threshold. For example, in the illustrated example, the interval L2 may be substantially longer than L1, indicating an increase in latency. Such an increase in latency may be indicative that loss of capture may occur if ATP therapy is not modified and processing circuitry may modify the ATP therapy accordingly. In other examples, interval L2 may be compared to another threshold such as an average interval between previous pacing pulses 440a-440d and respective evoked responses 442a-442d or the average plus an additional amount. Any suitable threshold may be used for comparison according to particular needs.

In some examples, the processing circuitry is further configured to determine the at least one latency metric by at least determining at least one morphological metric of an evoked response. For example, processing circuitry may determine latency metrics for one or more of evoked responses 442a-442e based on the morphology associated with the respective evoked response on an electrocardiogram illustrated in FIG. 11A. In some examples, the processing circuitry may interpret that the morphology associated with evoked response 442e indicates an increase in latency and may modify the ATP therapy accordingly.

In addition to being delayed after delivery of the pacing pulse, an evoked response that evidences increased latency may exhibit one or more characteristics morphological features, or changes in morphology, relative to non-delayed evoked responses. In some examples, processing circuitry may compare the morphology associated with evoked response 442e with a morphological template of morphological features associated with the presence or absence of increased latency to identify the increase in latency. The morphological template may be determined based on one or more morphological features, for example the maximum slew rate of the terminal portion of the evoked response or the post-stimulus time to peak amplitude, of one or more previous evoked responses, such as evoked responses 442a-442d.

Figure 12:
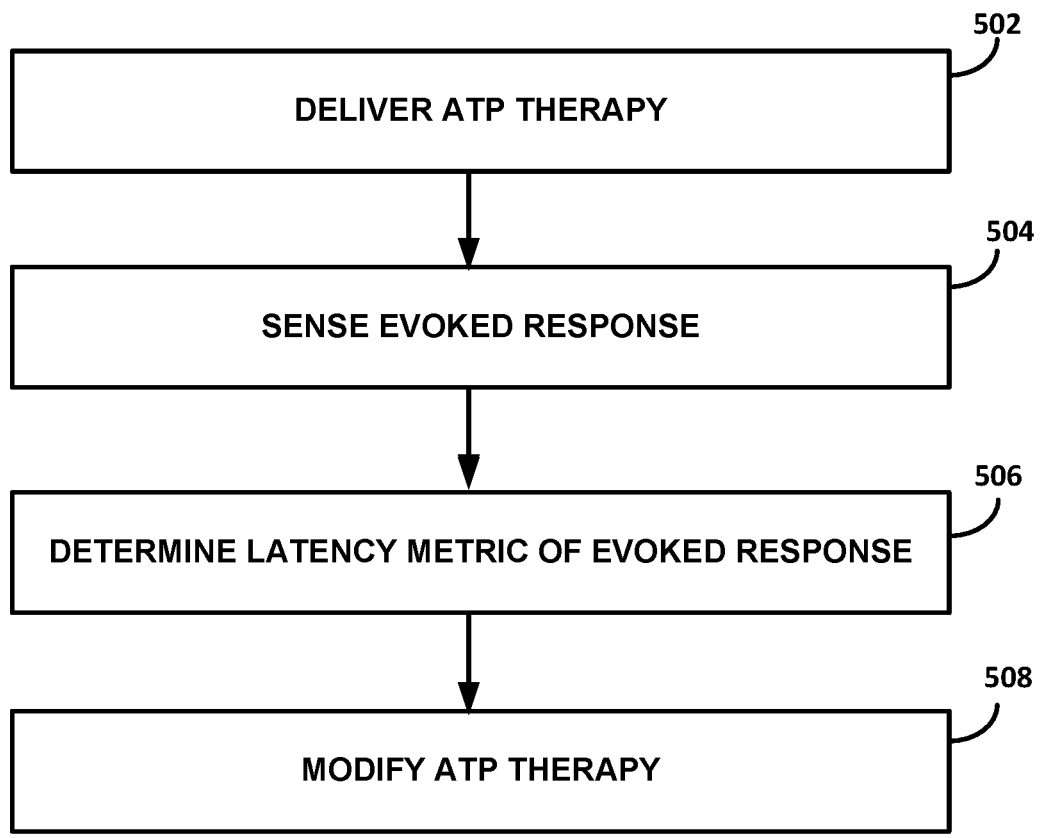
FIG. 12 is a flow diagram of an example process for modifying ATP therapy based on a determined latency metric.

FIG. 12 is a flow diagram of an example process for modifying ATP therapy based on a determined latency metric. Therapy delivery circuitry, such as the therapy delivery circuitry of one or more of the devices described above, may deliver anti-tachycardia pacing (ATP) therapy to heart 26 of a patient 14 (502). The ATP therapy may include one or more pulse trains and each of the one or more pulse trains may include a plurality of pacing pulses. Sensing circuitry, such as the sensing circuitry of one or more of the devices described above, may sense an evoked response of heart 26 to the pacing pulses (504).

During the delivery of the ATP therapy, processing circuitry, such as the processing circuitry of one or more of the devices described above, may, for at least one of the plurality of pacing pulses of at least one of the one or more pulse trains, determine at least one latency metric of an evoked response of heart 26 to the pacing pulse (506). In some examples, the latency metric may be an interval, as described in further detail below with reference to FIG. 13. In some examples, the processing circuitry may additionally or alternatively determine the at least one latency metric by at least one morphological metric of the evoked response. For example, the processing circuitry may determine the latency metric based on a morphology of one or more portions of an electrocardiogram, as described above with reference to FIG. 11A. The morphological metric may, for example, be indicative of an increase in latency.

In some examples, the processing circuitry may determine the at least one latency metric by determining, for at least one of the plurality of pacing pulses of at least one of the one or more pulse trains, a plurality of latency metrics of an evoked response of the heart to the pacing pulse.

For example, the processing circuitry may determine the at least one latency metric of the evoked response of the heart to the respective ones of the plurality of pacing pulses by determining an average value for a plurality of latency metrics corresponding to the plurality of the plurality of pacing pulses.

As another examples, the processing circuitry may determine a plurality of latency metrics, including two or more of a local latency metric based on an interval, a local latency metric based on a morphological characteristic, a global latency metric based on an interval, and/or a global latency metric based on a morphological characteristic, The processing circuitry may modify the ATP therapy based on the at least one latency metric (508). In some examples, the processing circuitry may modify the ATP therapy by modifying the ATP therapy based on a single of latency metric determined for a single delivered pulse, e.g., a comparison of an evoked response to a pacing pulse to a predetermined threshold that may be set, for example, by a clinician. In some examples, the processing circuitry may modify the ATP therapy by modifying the ATP therapy based on a plurality of latency metrics. For example, the processing circuitry may compare an average value for a plurality of latency metrics to a threshold and may modify the ATP if the average value exceeds the threshold. In some examples, the processing circuitry may modify the ATP therapy based on comparing multiple averages, e.g. comparing a short-term average to a long-term average.

In some examples, the processing circuitry may store, in a memory, such as the memory of any of the devices discussed above, ATP parameters that define the one or more pulse trains of the ATP therapy. The ATP therapy parameters may include cycle lengths of the plurality of pacing pulses of the pulse trains, a number of pulses of the pulse trains, and/or a pacing vector for delivery of the pulse trains. In some examples, the ATP therapy parameters specify that the one or more pulse trains each include one or more phases, with each of the phases including one or more pacing pulses, and successive phases having decreasing cycle lengths between pulses.

The processing circuitry may modify the ATP therapy by modifying such parameters for one or both of the current pulse train or a subsequent pulse train. In some examples, the processing circuitry may modify the plurality of the ATP parameters by increasing a cycle length of at least one pulse of the at least one, i.e. the current, pulse train, increasing or otherwise modifying a cycle length of at least one pulse of a subsequent pulse train, adding a pulse to the current pulse train, and/or modifying a pacing vector for delivery of a subsequent pulse train. In some examples, the ATP therapy parameters may define a first phase including a first subset of the plurality of pacing pulses having a first cycle length, and a second phase including a second subset of the plurality of pacing pulses having a second cycle length less than the first cycle length. In some examples, the processing circuitry may modify the at least one pulse train by modifying the ATP parameters that define the at least one pulse train by adding one or more pacing pulses having the first cycle length to the first phase, adding one or more pacing pulses having the second cycle length to the second phase, and/or adding an intermediate phase of one or more pulses between the first phase and the second phase, a cycle length of the one or more pacing pulses of the intermediate phase being between the first cycle length and the second cycle length.

In some examples, the ATP therapy parameters define a plurality of phases for the at least one pulse, each of the phases include a respective one or more pacing pulses having a common cycle length, and the common cycle lengths for the plurality of phases decrease from phase to phase. The processing circuitry may modify the at least one pulse train by advancing to a next one of the phases based on the at least one latency metric.

In some examples, the processing circuitry may advance to the next one of the phases by advancing to the next one of the phases in response to the latency metric being less than a threshold and/or a difference between the latency metric and a previous latency metric of a previous pulse of the at least one pulse train being less than a threshold.

Figure 13:
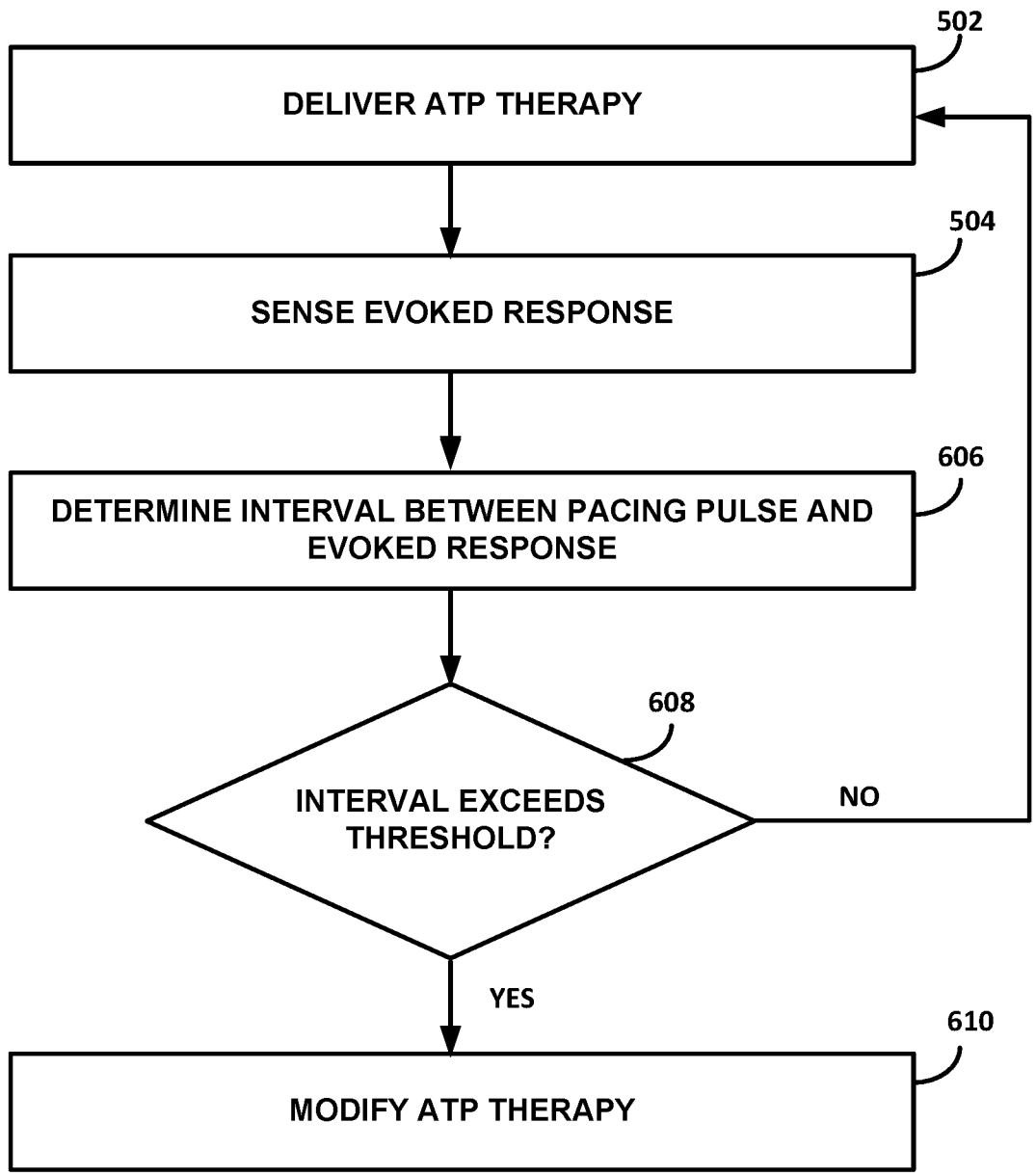
FIG. 13 is a flow diagram of an example process for modifying ATP therapy based on a determined latency metric including an interval between a pacing pulse and an evoked response.

FIG. 13 is a flow diagram of an example process for modifying ATP therapy based on a determined latency metric including an interval between a pacing pulse and an evoked response. As described above with reference to FIG. 12, therapy delivery circuitry may deliver ATP therapy to heart 26 of a patient 14 (502) and sensing circuitry may sense an evoked response of heart 26 to the pacing pulses of the ATP therapy (504).

The processing circuitry may determine the at least one latency metric by at least determining an interval between the pacing pulse and the evoked response (606), as described, for example, with reference to FIGS. 11A and 11B. The processing circuitry may compare the interval to a threshold to determine whether the interval exceeds the threshold (608). If the interval exceeds the threshold, the processing circuitry may modify the ATP therapy (610). If the interval does not exceed the threshold, the processing circuitry may continue to deliver ATP therapy (502).

In some examples, local and/or global latency metrics may be determined. Local latency metrics may be determined based on evoked responses sensed at or near a location of the delivery of the ATP therapy, e.g., using the same device and/or electrode vectors to delivery ATP therapy and sense the evoked response. Global latency metrics may be determined based on evoked responses sensed at a location at a substantial distance from the location of the delivery of the ATP therapy, e.g., using a different device and/or different electrode vectors using the same device to delivery ATP therapy and sense the evoked response. Local and global latency metrics may have different characteristics because areas of the heart further from the delivery of the of the ATP therapy may react differently to the ATP therapy than the area local to the ATP therapy delivery. In some examples, large-scale conduction delay may result in different local and global latency metrics because the heart may conduct the pacing pulse(s) locally but may not conduct the pacing pulse(s) as well across longer distances of the heart. This may indicate that modification to the ATP therapy may be needed to capture a sufficient area of the heart tissue to provide satisfactory therapy.

Figure 14:
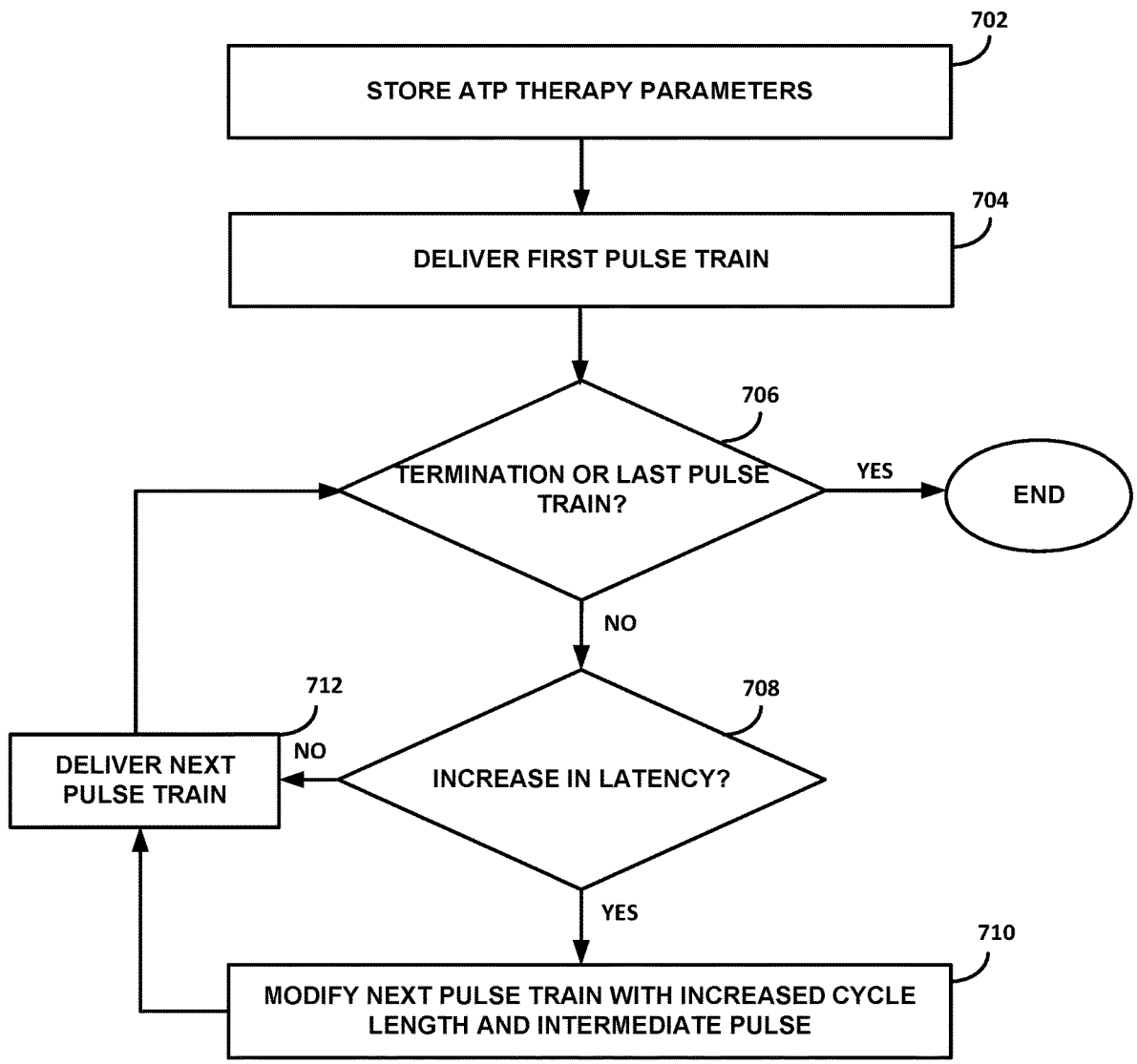
FIG. 14 is a flow diagram of an example process for modifying ATP therapy based on a determined latency metric including modifying a pulse train with an increased cycle length and an intermediate pulse.

FIG. 14 is a flow diagram of an example process for modifying ATP therapy based on a determined latency metric including modifying a pulse train with an increased cycle length and an intermediate pulse. Processing circuitry may store, in a memory, ATP parameters that define at least one pulse train and a subsequent pulse train of ATP therapy (702). Therapy delivery circuitry may deliver the at least one pulse train (704). Processing circuitry may determine whether the delivered pulse train is a termination or last pulse train (706), for example, based on stored ATP parameters. If it is, the process may end. If it is not, the processing circuitry may determine whether there has been an increase in latency (708). For example, the processing circuitry may determine one or more latency metrics, as described above with reference to FIGS. 11 and 12, to determine whether there has been an increase in latency. If the processing circuitry determines that there has not been an increase in latency, the processing circuitry may deliver the next pulse train (712).

If the processing circuitry determines that there has been an increase in latency, the processing circuitry may modify at least one of the ATP parameters that defines the subsequent pulse train (710) prior to the therapy delivery circuitry delivering the subsequent pulse train (712).

In some examples, the ATP parameters that define the subsequent pulse train may include a cycle length of one or more of the plurality of pacing pulses of the subsequent pulse train and the processing circuitry is may modify the ATP parameter that defines the subsequent pulse train by increasing the cycle length. In some examples, the processing circuitry may increase the cycle length from a first value that is less than a corresponding cycle length of one or more pacing pulses of the at least one pulse train to a second value that is greater than the corresponding cycle length of the one or more pacing pulses of the at least one pulse train.

In some examples, the ATP parameters that define the at least one pulse train and the subsequent pulse train comprise at least one ATP parameter that specifies a pacing vector for delivery of the at least one pulse train and the subsequent pulse train. For example, the ATP parameters may specify the pacing vector by specifying a combination of electrodes of the one or more devices described above for delivery of the at least one pulse train and the subsequent pulse train. The processing circuitry may modify the at least one of the ATP parameters that define the subsequent pulse train by specifying a different pacing vector for delivery of the subsequent pulse train. For example, the processing circuitry may specify a different combination of electrodes of the one or more devices described above for delivery of the subsequent pulse train.

After delivery of the subsequent pulse train (712), the processing circuitry may again determine whether the delivered pulse train is a termination or last pulse train (706) and the process may continue until the processing circuitry determines that the most recently delivered pulse train is a termination or last pulse train (706).

Figure 15:
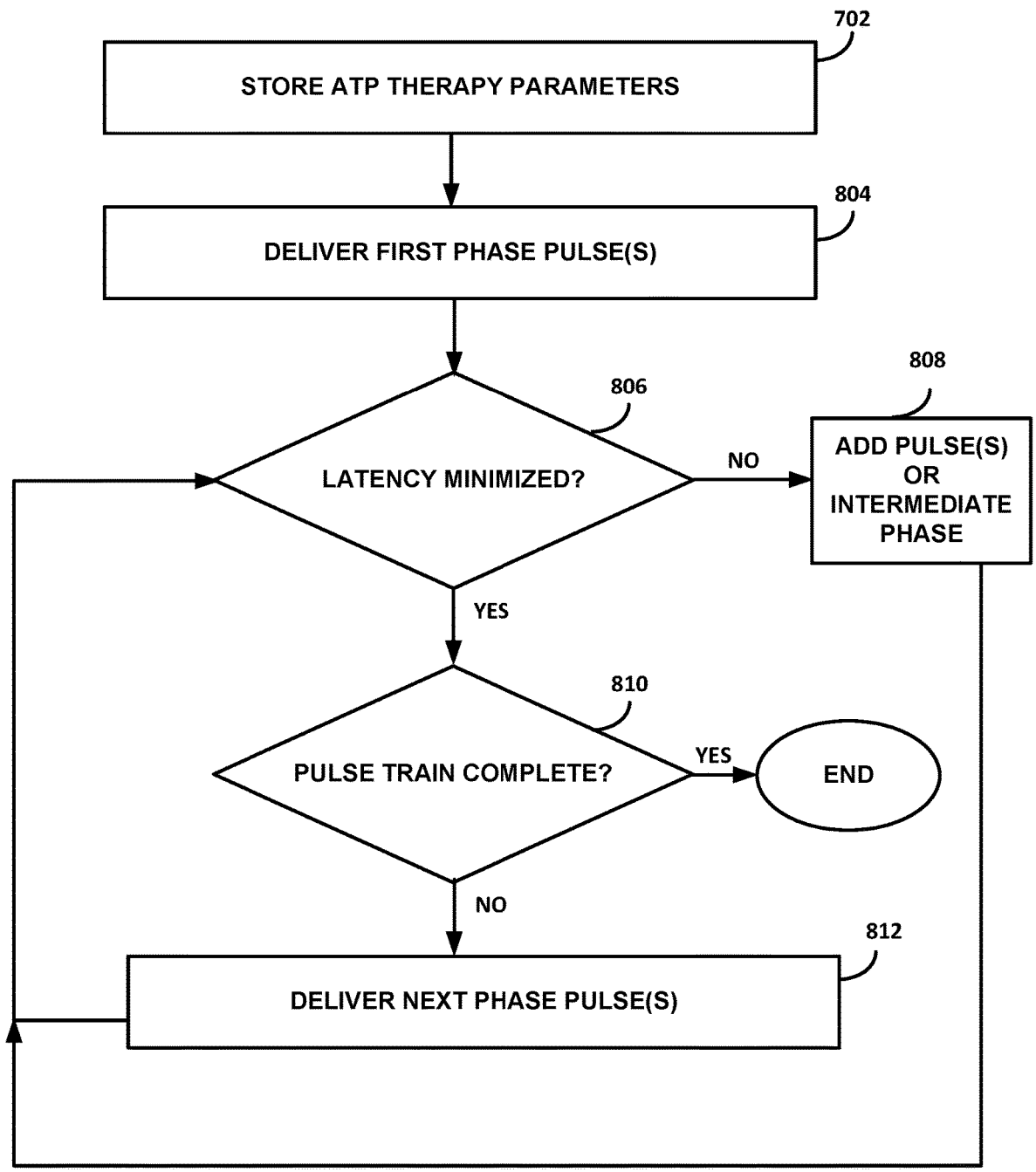
FIG. 15 is a flow diagram of an example process for modifying ATP therapy based on a determined latency metric by adding an additional pulses or an intermediate phase to a pulse train.

FIG. 15 is a flow diagram of an example process for modifying ATP therapy based on a determined latency metric by adding an additional pulses or an intermediate phase to a pulse train. Processing circuitry may store, in a memory, ATP parameters that define at least one pulse train and a subsequent pulse train of ATP therapy (702). The ATP parameters that define the subsequent pulse train may include ATP parameters that define a first phase comprising a first subset of the plurality of pacing pulses having a first cycle length, and a second phase comprising a second subset of the plurality of pacing pulses having a second cycle length less than the first cycle length.

Therapy delivery circuitry may deliver the first phase pulse(s) (804). Processing circuitry may determine whether latency has been minimized (806), for example, based on determined latency metrics for pulses in the first phase. If the processing circuitry determines that latency has not been minimized, the processing circuitry may modify at least one of the ATP parameters that define the subsequent pulse train by adding one or more pacing pulses having the first cycle length to the first phase, adding one or more pacing pulses having the second cycle length to the second phase, and/or adding an intermediate phase comprising one or more pulses between the first phase and the second phase, a cycle length of the one or more pacing pulses of the intermediate phase being between the first cycle length and the second cycle length (808). The therapy delivery circuitry may then deliver the next phase pulse(s) (812) and the processing circuitry may again determine whether latency has been minimized (806). This series of steps may continue until the processing circuitry determines that latency is minimized.

If the processing circuitry determines that latency has been minimized, the processing circuitry may determine whether the pulse train is complete (810). If the processing circuitry determines that the pulse train is complete, the process may end. If the processing circuitry does not determine that the pulse train is complete, the therapy delivery circuitry may deliver the next phase pulse(s) 812 and the processing circuitry may determine whether latency is minimized (806) and, if so, whether the pulse train is complete. This process may continue until latency is minimized and the pulse train is complete.

Figure 16:
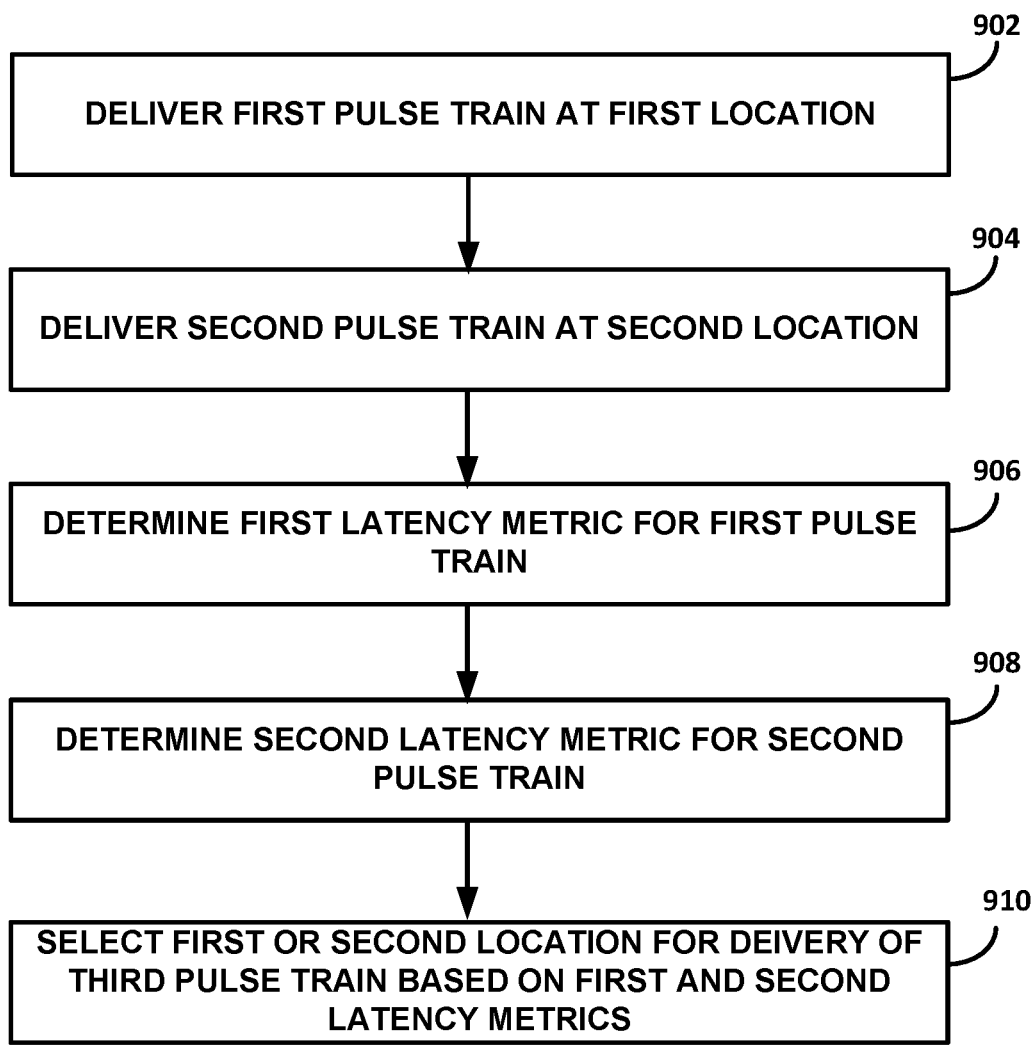
FIG. 16 is a flow diagram of an example process for modifying ATP therapy based on a determined latency metric by selecting a location for delivery of a pulse train based on determined latency metrics.

FIG. 16 is a flow diagram of an example process for modifying ATP therapy based on a determined latency metric by selecting a location for delivery of a pulse train based on determined latency metrics. The process may include determining a latency metric for a first pulse train delivered at a first location, determining a latency metric for a second pulse train delivered at a second location, and selecting the first or second location for delivery of a third pulse train based on the latency metrics.

In some examples, the therapy delivery circuitry may deliver the ATP therapy by delivering a first pulse train of the one or more pulse trains to a first location of the heart (902) and delivering a second pulse train of the one or more pulse trains to a second location of the heart (904). In some examples, the processing circuitry may determine the at least one latency metric by determining at least a first latency metric for the first pulse train (906) and second latency metric for the second pulse train (908). In some examples, the processing circuitry may modify the ATP therapy by selecting one of the first location or the second location for delivery of a third pulse train of the one or more pulse trains based on the first latency metric and the second latency metric (910). For example, the processing circuitry may choose which of the two locations result in the best therapy performance based on the latency metrics for the two locations. Any combination of therapy circuitry and/or processing circuitry of the devices described above may be used for any of the steps described above. For example, different therapy delivery circuitry of different devices may be used to delivery the first and second pulse trains to different locations.

In some examples, the processing circuitry may further determine latency metrics based on pulses delivered at different locations and/or evoked responses sensed at different locations of the heart.

In some examples, the therapy delivery circuitry may deliver the ATP therapy by delivering the at least one pacing pulse to a first location of the heart. For example, the therapy delivery circuitry may be in any of the devices of discussed above and may deliver the at least one pacing pulse via any of the electrodes discussed above. The processing circuitry, which may be the processing circuitry of any of the devices above, may determine the at least one latency metric of the evoked response of the heart to the pacing pulse by at least determining a local latency metric based on sensing the evoked response at one of the first location or a second location of the heart and/or determining a large scale latency metric based on sensing the evoked response at a third location, wherein the third location is located further from the first location than the second location. By determining a local latency metric based on the evoked response sensed at or close to the location of the delivery of ATP therapy and the large scale latency metric based on the evoked response sensed further from the location of the delivery of ATP therapy, the processing circuitry and/or a user may compare how the ATP therapy is affecting different portions of the heart, whether close to or further from the delivery of the ATP therapy.

The processing circuitry may determine the local latency metric and/or the large scale latency metric in any suitable manner. In some examples, the processing circuitry may determine the local latency metric by determining an interval between the pacing pulse and the evoked response at the one of the first location or a second location and/or determining at least one morphological metric of the evoked response at the one of the first location or a second location. In some examples, the processing circuitry may determine the large scale latency metric by determining an interval between the pacing pulse and the evoked response at the third location and/or determining at least one morphological metric of the evoked response at third location.

In some examples, the processing circuitry may determine the at least one latency metric by determining, for at least one of the plurality of pacing pulses of at least one of the one or more pulse trains, a plurality of latency metrics of an evoked response of the heart to the pacing pulse. In some examples, the plurality of latency metrics may include the interval between the pacing pulse and the evoked response at the one of the first location or a second location and/or the at least one morphological metric of the evoked response at the one of the first location or a second location. In some examples, the processing circuitry is further may determine the large scale latency metric by the interval between the pacing pulse and the evoked response at the third location and/or the least one morphological metric of the evoked response at third location. In some examples, the processing circuitry may modify the ATP therapy by modifying the ATP therapy based on the plurality of latency metrics.

In some examples, the processing circuitry may modify the ATP therapy by delivering a subsequent pulse train of the one or more pulse trains at a fourth location of the heart that is different than the first location. For example, the processing circuitry may determine that the local latency and/or large scale latency indicate poor performance of therapy delivery at the first location such that the processing circuitry my modify the therapy to deliver a subsequent pulse train at a different location, which may result in better performance than delivery at the first location.

Any suitable modifications may be made to the processes described herein and any suitable device, processing circuitry, therapy delivery circuitry, and/or electrodes may be used for performing the steps of the methods described herein. The steps the methods may be performed by any suitable number of devices. For example, a processing circuitry of one device may perform some of the steps while a therapy delivery circuitry and/or sensing circuitry of another device may perform other steps of the method, while communication circuitry may allow for communication needed for the processing circuitry to receive information from other devices. This coordination may be performed in any suitable manner according to particular needs.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to ICD 9, IPD 16, PCD 110, external device 21, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between ICD 9, IPD 16, PCD 110, and/or external device 21. In addition, any of the described units, circuitry or components may be implemented together or separately as discrete but interoperable logic devices. Depiction of different features as circuitry is intended to highlight different functional aspects and does not necessarily imply that such circuitry must be realized by separate hardware or software components. Rather, functionality associated with one or more circuitry may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

As used herein, the term "circuitry" refers to an application specific integrated circuit (ASIC), an electronic circuit, a processor (shared, dedicated, or group) and memory that execute one or more software or firmware programs, a combinational logic circuit, or other suitable components that provide the described functionality.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described for delivering cardiac stimulation therapies as well as coordinating the operation of various devices within a patient. Any combination of the described operations or functions is contemplated. These and other examples are within the scope of the following claims.

What is claimed is:

1. A method comprising:
    delivering anti-tachycardia pacing (ATP) therapy to a heart of a patient according to a set of ATP parameters that define a sequence for delivery of a plurality of pacing pulses as one or more pulse trains, the sequence configured to terminate a tachyarrhythmia, each of the one or more pulse trains comprising one or more of the plurality of pacing pulses, the ATP therapy including at least a first pulse train of the one or more pulse trains;
    for at least one or more pacing pulses of the first pulse train, determining at least one latency metric of an evoked response of the heart to the one or more pacing pulses of the first pulse train; and
    modifying one or more ATP parameters of the set of ATP parameters based on the at least one latency metric.

2. The method of claim 1, wherein determining the at least one latency metric comprises determining at least one morphological metric of the evoked response.

3. The method of claim 1, wherein determining the at least one latency metric comprises determining an interval between the one or more pacing pulses of the first pulse train and the evoked response.

4. The method of claim 1, wherein the sequence comprises a series of cycle lengths for the plurality of pacing pulses configured to terminate the tachyarrhythmia.

5. The method of claim 1, wherein the one or more pulse trains comprise a plurality of pulse trains, and wherein modifying the one or more ATP parameters comprises modifying at least one of the ATP parameters that define a subsequent pulse train prior to delivery of the subsequent pulse train.

6. The method of claim 5, wherein modifying the at least one of the ATP parameters that define the subsequent pulse train comprises modifying a common cycle length of the one or more pacing pulses of the subsequent pulse train prior to delivery of the one or more pacing pulses of the subsequent pulse train.

7. The method of claim 5,
    wherein the ATP parameters that define the subsequent pulse train include a cycle length of one or more of a plurality of pacing pulses of the subsequent pulse train, and
    wherein modifying the at least one of the ATP parameters that define the subsequent pulse train comprises increasing the cycle length of the one or more of the plurality of pacing pulses of the subsequent pulse train.

8. The method of claim 7, wherein increasing the cycle length of the one or more of the plurality of pacing pulses of the subsequent pulse train comprises increasing the cycle length from a first value that is less than a corresponding cycle length of one or more pacing pulses of the first pulse train to a second value that is greater than the corresponding cycle length of the one or more pacing pulses of the first pulse train.

9. The method of claim 5,
    wherein the ATP parameters that define the at least one first pulse train and the subsequent pulse train comprise at least one ATP parameter that specifies a pacing vector for delivery of the at least one first pulse train and the subsequent pulse train, and
    wherein modifying the at least one of the ATP parameters that define the subsequent pulse train comprises specifying a different pacing vector for delivery of the subsequent pulse train.

10. The method of claim 5, wherein the one or more pacing pulses of the subsequent pulse train comprise a plurality of pacing pulses,
    wherein the ATP parameters define a first phase comprising one or more first pacing pulses of the plurality of pacing pulses, the one or more first pacing pulses having a first cycle length, and a second phase comprising one or more second pacing pulses of the plurality of pacing pulses, the one or more second pacing pulses having a second cycle length that is less than the first cycle length,
    wherein modifying the subsequent pulse train comprises modifying the ATP parameters that define the subsequent pulse train comprises at least one of:
        adding one or more pacing pulses having the first cycle length to the first phase,
        adding one or more pacing pulses having the second cycle length to the second phase, or
        adding an intermediate phase comprising one or more pulses between the first phase and the second phase, a cycle length of the one or more pacing pulses of the intermediate phase being between the first cycle length and the second cycle length.

11. The method of claim 1, wherein delivering the ATP therapy comprises delivering the first pulse train to a first location of the heart, the method further comprising:
    comparing the at least one latency metric to a threshold; and
    determining that a latency metric of the at least one latency metric satisfies the threshold,
    wherein modifying the one or more ATP parameters based on the at least one latency metric comprises delivering a subsequent pulse train of the one or more pulse trains to a second location of the heart based on determining that the latency metric of the at least one latency metric satisfies the threshold.

12. The method of claim 1, wherein modifying the one or more ATP parameters comprises modifying at least one of the ATP parameters that defines the first pulse train.

13. The method of claim 12, wherein modifying the at least one of the ATP parameters that define the first pulse train comprises modifying a common cycle length of the one or more pacing pulses of first pulse train prior to delivery of the one or more pacing pulses of the first pulse train.

14. The method of claim 12, wherein the one or more pacing pulses of the first pulse train comprise a plurality of pacing pulses,
wherein the ATP parameters define a first phase comprising one or more first pacing pulses of the plurality of pacing pulses, the one or more first pacing pulses having a first cycle length, and a second phase comprising one or more second pacing pulses of the plurality of pacing pulses, the one or more second pacing pulses having a second cycle length that is less than the first cycle length, and
wherein modifying the first pulse train comprises modifying the ATP parameters that define the first pulse train comprises at least one of:
adding one or more pacing pulses having the first cycle length to the first phase,
adding one or more pacing pulses having the second cycle length to the second phase, or
adding an intermediate phase comprising one or more pulses between the first phase and the second phase, a cycle length of the one or more pacing pulses of the intermediate phase being between the first cycle length and the second cycle length.

15. The method of claim 14,
wherein each of the one or more pulse trains defines one or more phases,
wherein each of the one or more phases includes at least one of the one or more pacing pulses having a common cycle length corresponding to the phase, and
wherein modifying the first pulse train comprises advancing to a next one of the one or more phases based on the at least one latency metric.

16. The method of claim 15, wherein advancing to the next one of the phases comprises advancing to the next one of the phases in response to at least one of:
a latency metric of the at least one latency metric not satisfying a threshold, or
a difference between the latency metric and a previous latency metric of a previous pulse of the one or more pulse trains not satisfying a latency metric difference threshold.

17. The method of claim 1,
wherein delivering the ATP therapy comprises delivering the one or more pacing pulses of the first pulse train to a first location of the heart;
wherein determining the at least one latency metric of the evoked response of the heart to the one or more pacing pulses of the first pulse train comprises at least one of:
determining a local latency metric based on sensing the evoked response at one of the first location or a second location of the heart, or
determining a large-scale latency metric based on sensing the evoked response at a third location, wherein the third location is located further from the first location than the second location.

18. The method of claim 17, wherein
determining the local latency metric comprises at least one of:
determining an interval between a pacing pulse of the one or more pacing pulses of the first pulse train and the evoked response at the one of the first location or a second location, and
determining at least one morphological metric of the evoked response at the one of the first location or a second location, and
determining the large-scale latency metric comprises at least one of:
determining an interval between the pacing pulse of the one or more pacing pulses of the first pulse train and the evoked response at the third location, and
determining at least one morphological metric of the evoked response at third location.

19. A medical device comprising:
therapy delivery circuitry configured to deliver anti-tachycardia pacing (ATP) therapy to a heart of a patient; and
processing circuitry configured to:
control the therapy delivery circuitry to deliver ATP therapy to the heart of the patient according to a set of ATP parameters that define a sequence for delivery of a plurality of pacing pulses as one or more pulse trains, the sequence configured to terminate a tachyarrhythmia, each of the one or more pulse trains comprising one or more of the plurality of pacing pulses, the ATP therapy including at least a first pulse train of the one or more pulse trains;
for at least one or more pacing pulses of the first pulse train, determine at least one latency metric of an evoked response of the heart to the one or more pacing pulses of the first pulse train; and
modify one or more ATP parameters of the set of ATP parameters based on the at least one latency metric.

20. The medical device of claim 19, wherein the processing circuitry is configured to determine the at least one latency metric by at least determining at least one morphological metric of the evoked response.

21. The medical device of claim 19, wherein the processing circuitry is configured to determine the at least one latency metric by at least determining an interval between the one or more pacing pulses of the first pulse train and the evoked response.

22. The medical device of claim 19, wherein the sequence comprises a series of cycle lengths for the plurality of pacing pulses configured to terminate the tachyarrhythmia.

23. The medical device of claim 19, wherein the one or more pulse trains comprise a plurality of pulse trains, and wherein the processing circuitry is configured to modify the one or more ATP parameters by at least modifying at least one of the ATP parameters that define a subsequent pulse train prior to delivery of the subsequent pulse train.

24. The medical device of claim 23, wherein the processing circuitry is configured to modify the at least one of the ATP parameters that define the subsequent pulse train comprises by at least modifying a common cycle length of the one or more pacing pulses of the subsequent pulse train prior to delivery of the one or more pacing pulses of the subsequent pulse train.

25. The medical device of claim 23,
wherein the ATP parameters that define the subsequent pulse train include a cycle length of one or more of a plurality of pacing pulses of the subsequent pulse train, and
wherein the processing circuitry is configured to modify the at least one of the ATP parameters that define the subsequent pulse train by at least increasing the cycle length of the one or more of the plurality of pacing pulses of the subsequent pulse train.

26. The medical device of claim 25, wherein the processing circuitry is configured to increase the cycle length of the one or more of the plurality of pacing pulses of the subsequent pulse train by at least increasing the cycle length from a first value that is less than a corresponding cycle length of one or more pacing pulses of the first pulse train to a second value that is greater than the corresponding cycle length of the one or more pacing pulses of the first pulse train.

27. The medical device of claim 23,
wherein the ATP parameters that define the at least one first pulse train and the subsequent pulse train comprise at least one ATP parameter that specifies a pacing vector for delivery of the at least one first pulse train and the subsequent pulse train, and
wherein the processing circuitry is configured to modify the at least one of the ATP parameters that define the subsequent pulse train by at least specifying a different pacing vector for delivery of the subsequent pulse train.

28. The medical device of claim 23, wherein the one or more pacing pulses of the subsequent pulse train comprise a plurality of pacing pulses,
wherein the ATP parameters define a first phase comprising one or more first pacing pulses of the plurality of pacing pulses, the one or more first pacing pulses having a first cycle length, and a second phase comprising one or more second pacing pulses of the plurality of pacing pulses, the one or more second pacing pulses having a second cycle length that is less than the first cycle length,
wherein the processing circuitry is configured to modify the subsequent pulse train by at least modifying the ATP parameters that define the subsequent pulse train by at least one of:
adding one or more pacing pulses having the first cycle length to the first phase,
adding one or more pacing pulses having the second cycle length to the second phase, or
adding an intermediate phase comprising one or more pulses between the first phase and the second phase, a cycle length of the one or more pacing pulses of the intermediate phase being between the first cycle length and the second cycle length.

29. The medical device of claim 19, wherein the processing circuitry is configured to control the therapy delivery circuitry to deliver the ATP therapy by at least controlling the therapy delivery circuitry to deliver the first pulse train to a first location of the heart, wherein the processing circuitry is further configured to:
compare the at least one latency metric to a threshold; and
determine that a latency metric of the at least one latency metric satisfies the threshold,
wherein the processing circuitry is configured to modify the one or more ATP parameters based on the at least one latency metric by at least controlling the therapy delivery circuitry to deliver a subsequent pulse train of the one or more pulse trains to a second location of the heart based on determining that the latency metric of the at least one latency metric satisfies the threshold.

30. The medical device of claim 19, wherein the processing circuitry is configured to modify the one or more ATP parameters by at least modifying at least one of the ATP parameters that defines the first pulse train.

31. The medical device of claim 30, wherein the processing circuitry is configured to modify the at least one of the ATP parameters that define the first pulse train by at least modifying a common cycle length of the one or more pacing pulses of first pulse train prior to delivery of the one or more pacing pulses of the first pulse train.

32. The medical device of claim 30, wherein the one or more pacing pulses of the first pulse train comprise a plurality of pacing pulses,
wherein the ATP parameters define a first phase comprising one or more first pacing pulses of the plurality of pacing pulses, the one or more first pacing pulses having a first cycle length, and a second phase comprising one or more second pacing pulses of the plurality of pacing pulses, the one or more second pacing pulses having a second cycle length that is less than the first cycle length, and
wherein the processing circuitry is configured to modify the first pulse train by at least modifying the ATP parameters that define the first pulse train by at least one of:
adding one or more pacing pulses having the first cycle length to the first phase,
adding one or more pacing pulses having the second cycle length to the second phase, or
adding an intermediate phase comprising one or more pulses between the first phase and the second phase, a cycle length of the one or more pacing pulses of the intermediate phase being between the first cycle length and the second cycle length.

33. The medical device of claim 32,
wherein each of the one or more pulse trains defines one or more phases,
wherein each of the one or more phases includes at least one of the one or more pacing pulses having a common cycle length corresponding to the phase, and
wherein the processing circuitry is configured to modify the first pulse train by at least advancing to a next one of the one or more phases based on the at least one latency metric.

34. The medical device of claim 33, wherein the processing circuitry is configured to advance to the next one of the phases by at least advancing to the next one of the phases in response to at least one of:
a latency metric of the at least one latency metric not satisfying a threshold, or
a difference between the latency metric and a previous latency metric of a previous pulse of the one or more pulse trains not satisfying a latency metric difference threshold.

35. The medical device of claim 19,
wherein the processing circuitry is configured to control the therapy delivery circuitry to deliver the ATP therapy by at least controlling the therapy delivery circuitry to deliver the one or more pacing pulses of the first pulse train to a first location of the heart;
wherein the processing circuitry is configured to determine the at least one latency metric of the evoked response of the heart to the one or more pacing pulses of the first pulse train by at least one of:
determining a local latency metric based on sensing the evoked response at one of the first location or a second location of the heart, or
determining a large-scale latency metric based on sensing the evoked response at a third location, wherein the third location is located further from the first location than the second location.

36. The medical device of claim 35, wherein
the processing circuitry is configured to determine the local latency metric by at least one of:

determining an interval between a pacing pulse of the one or more pacing pulses of the first pulse train and the evoked response at the one of the first location or a second location, and determining at least one morphological metric of the evoked response at the one of the first location or a second location, and determining the large-scale latency metric comprises at least one of:

determining an interval between the pacing pulse of the one or more pacing pulses of the first pulse train and the evoked response at the third location, and determining at least one morphological metric of the evoked response at third location.

37. A non-transitory computer-readable medium storing instructions for causing processing circuitry to perform a method comprising:

controlling therapy delivery circuitry to deliver anti-tachycardia pacing (ATP) therapy to a heart of a patient according to a set of ATP parameters that define a sequence for delivery of a plurality of pacing pulses as one or more pulse trains, the sequence configured to terminate a tachyarrhythmia, each of the one or more pulse trains comprising one or more of the plurality of pacing pulses, the ATP therapy including at least a first pulse train of the one or more pulse trains;

for at least one or more pacing pulses of the first pulse train, determining at least one latency metric of an evoked response of the heart to the one or more pacing pulses of the first pulse train; and modifying one or more ATP parameters of the set of ATP parameters based on the at least one latency metric.

38. The non-transitory computer-readable medium of claim 37, wherein the instructions cause the processing circuitry to control the therapy delivery circuitry to deliver the ATP therapy by at least controlling the therapy delivery circuitry to deliver the first pulse train to a first location of the heart, the method further comprising:

comparing the at least one latency metric to a threshold; and determining that a latency metric of the at least one latency metric satisfies the threshold, wherein modifying the one or more ATP parameters based on the at least one latency metric comprises delivering a subsequent pulse train of the one or more pulse trains to a second location of the heart based on determining that the latency metric of the at least one latency metric satisfies the threshold.

* * * * *